US009585591B2

(12) United States Patent
Morikawa et al.

(10) Patent No.: US 9,585,591 B2
(45) Date of Patent: Mar. 7, 2017

(54) ELECTRONIC DEVICE, INFORMATION PROCESSING APPARATUS, INFORMATION PROCESSING METHOD AND PROGRAM

(71) Applicant: Panasonic Corporation, Osaka (JP)

(72) Inventors: Koji Morikawa, Kyoto (JP); Akinori Matsumoto, Osaka (JP); Jeffry Bonar Fernando, Osaka (JP); Katsuyoshi Yamagami, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/273,800

(22) Filed: May 9, 2014

(65) Prior Publication Data

US 2014/0249438 A1     Sep. 4, 2014

Related U.S. Application Data

(63) Continuation of application No. PCT/JP2013/005347, filed on Sep. 10, 2013.

(30) Foreign Application Priority Data

Sep. 10, 2012    (JP) ................................ 2012-198235

(51) Int. Cl.
*A61B 5/0456*      (2006.01)
*A61B 5/0408*      (2006.01)
(Continued)

(52) U.S. Cl.
CPC .......... *A61B 5/0456* (2013.01); *A61B 5/0015* (2013.01); *A61B 5/0452* (2013.01);
(Continued)

(58) Field of Classification Search
CPC .... A61B 5/6898; A61B 5/0404; A61B 5/0402
See application file for complete search history.

(56) References Cited

U.S. PATENT DOCUMENTS

2001/0034491 A1    10/2001   Benson et al.

FOREIGN PATENT DOCUMENTS

| JP | 2002-233513 A | 8/2002 |
| JP | 2003-333403 A | 11/2003 |

(Continued)

OTHER PUBLICATIONS

International Search Report for corresponding International Application No. PCT/JP2013/005347 mailed Dec. 17, 2013.

*Primary Examiner* — Carl H Layno
*Assistant Examiner* — Jennifer Ghand
(74) *Attorney, Agent, or Firm* — Renner, Otto, Boisselle & Sklar, LLP

(57) ABSTRACT

An exemplary electronic device is in a housing to be gripped by a right hand and a left hand of a user, and has a plurality of manipulable portions. The electronic device includes: electrodes placed at positions which come in contact with the right hand and left hand of the user gripping the housing; an extractor for extracting an electrocardiographic component of the user from a potential difference between the electrodes; a determination section for determining whether the extracted electrocardiographic component is in a positive direction or a negative direction by referring to a prestored criterion; and a change section for, in accordance with a result of determination by the determination section, changing assignment between each of the plurality of manipulable portions and a manipulation signal generated in response to a manipulation.

15 Claims, 27 Drawing Sheets

(51) Int. Cl.
    *A61B 5/0452*     (2006.01)
    *A61B 5/00*     (2006.01)
    *G06F 1/16*     (2006.01)
    *G06F 3/01*     (2006.01)

(52) U.S. Cl.
    CPC ........ *A61B 5/04085* (2013.01); *G06F 1/1684* (2013.01); *G06F 3/015* (2013.01); *A61B 2560/0468* (2013.01)

(56) References Cited

FOREIGN PATENT DOCUMENTS

| | | |
|---|---|---|
| JP | 2004-078634 A | 3/2004 |
| JP | 2007-046906 A | 2/2007 |
| JP | 2009-261723 A | 11/2009 |
| JP | 2011-147582 A | 8/2011 |
| JP | 2012-029845 A | 2/2012 |

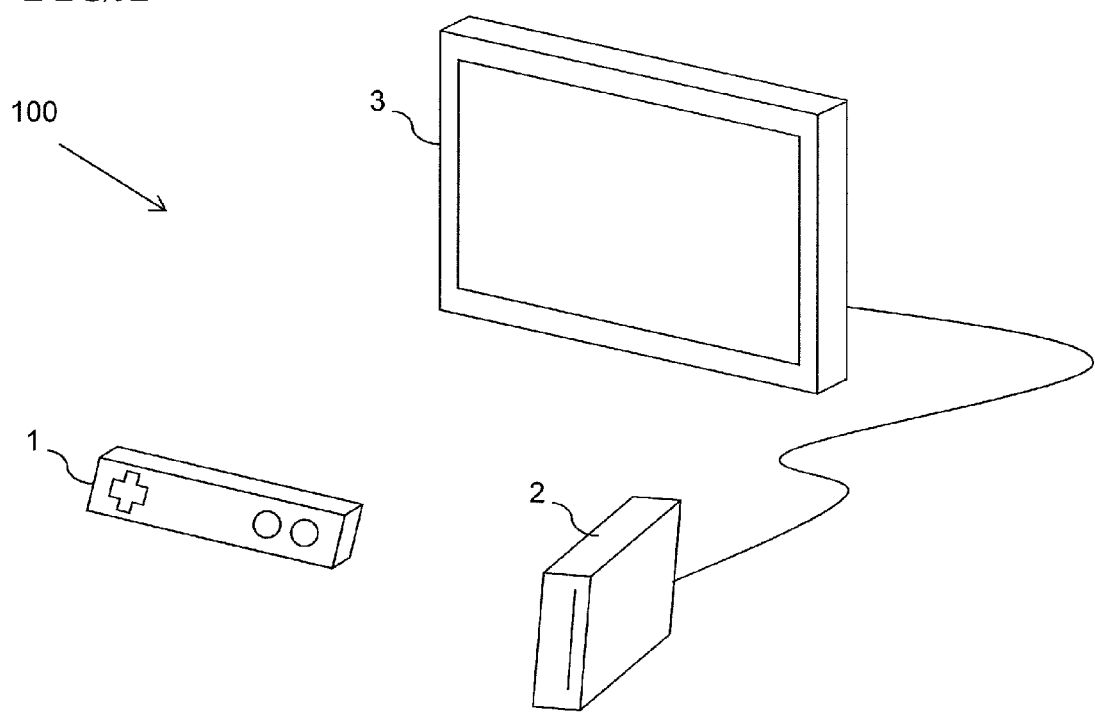

FIG.4A
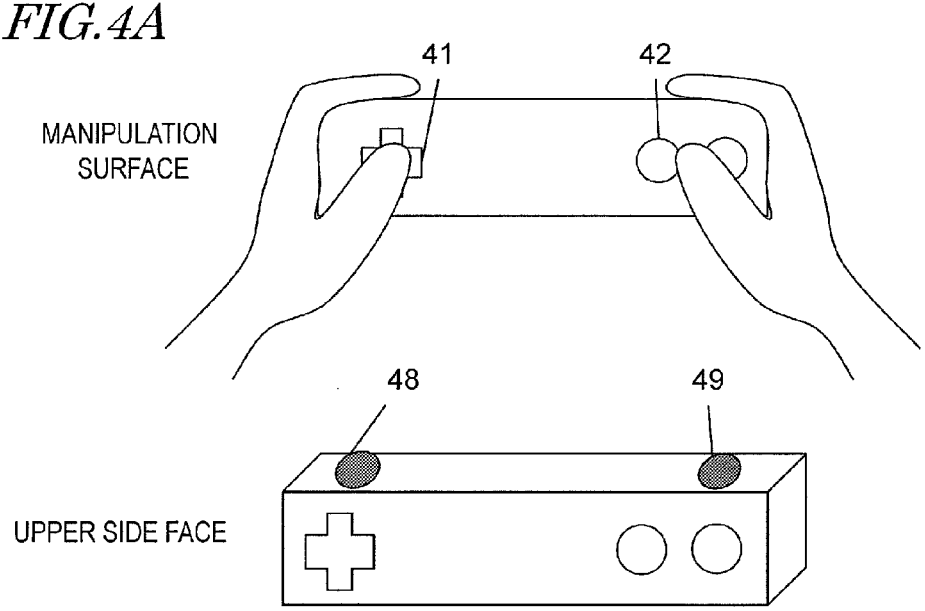
MANIPULATION SURFACE
UPPER SIDE FACE
FIG.4B
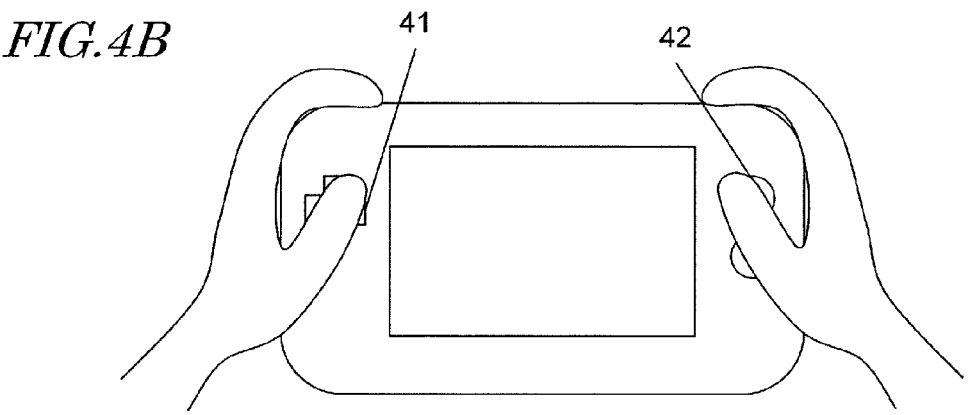
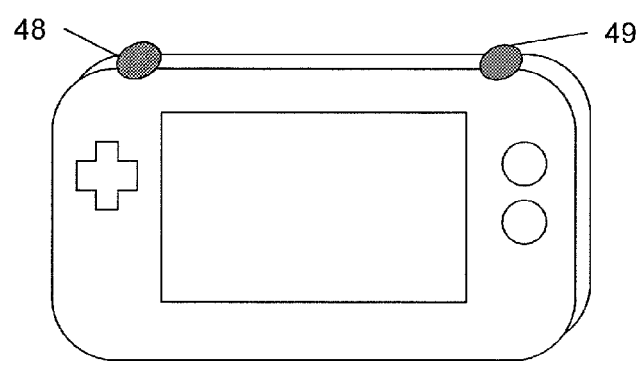

FIG.5
(a)
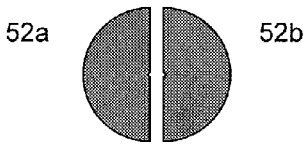
(b)
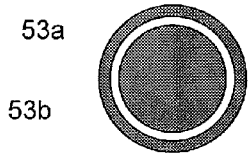
(c)
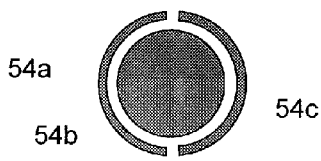
(d)
FIG.6A
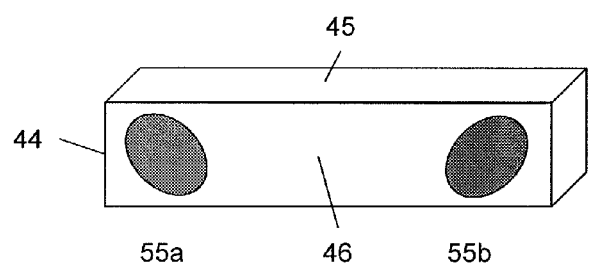
FIG.6B
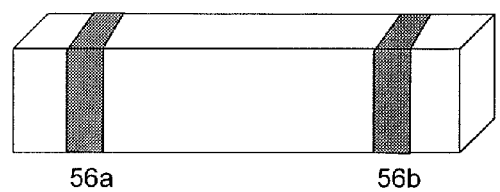
FIG.6C
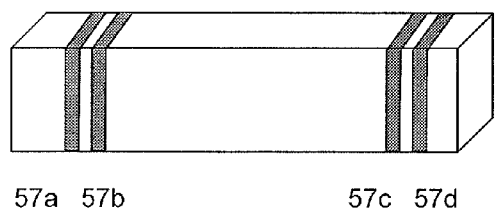

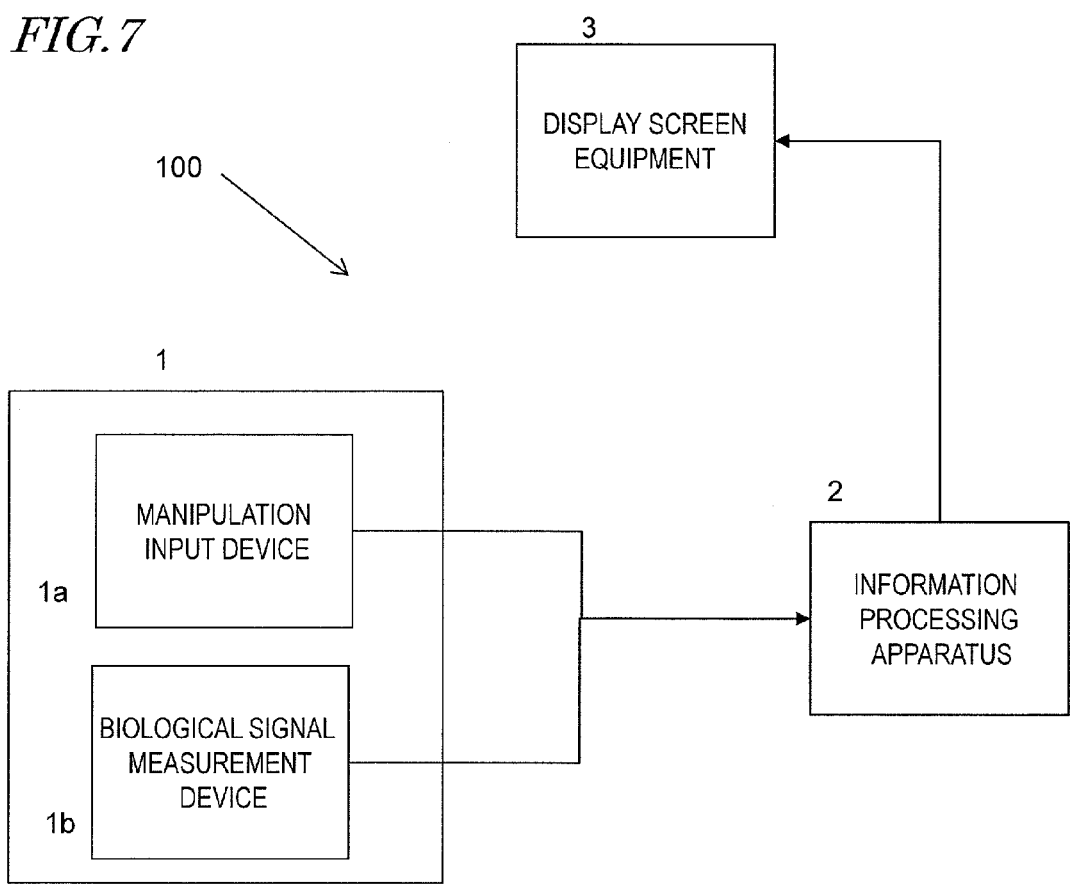

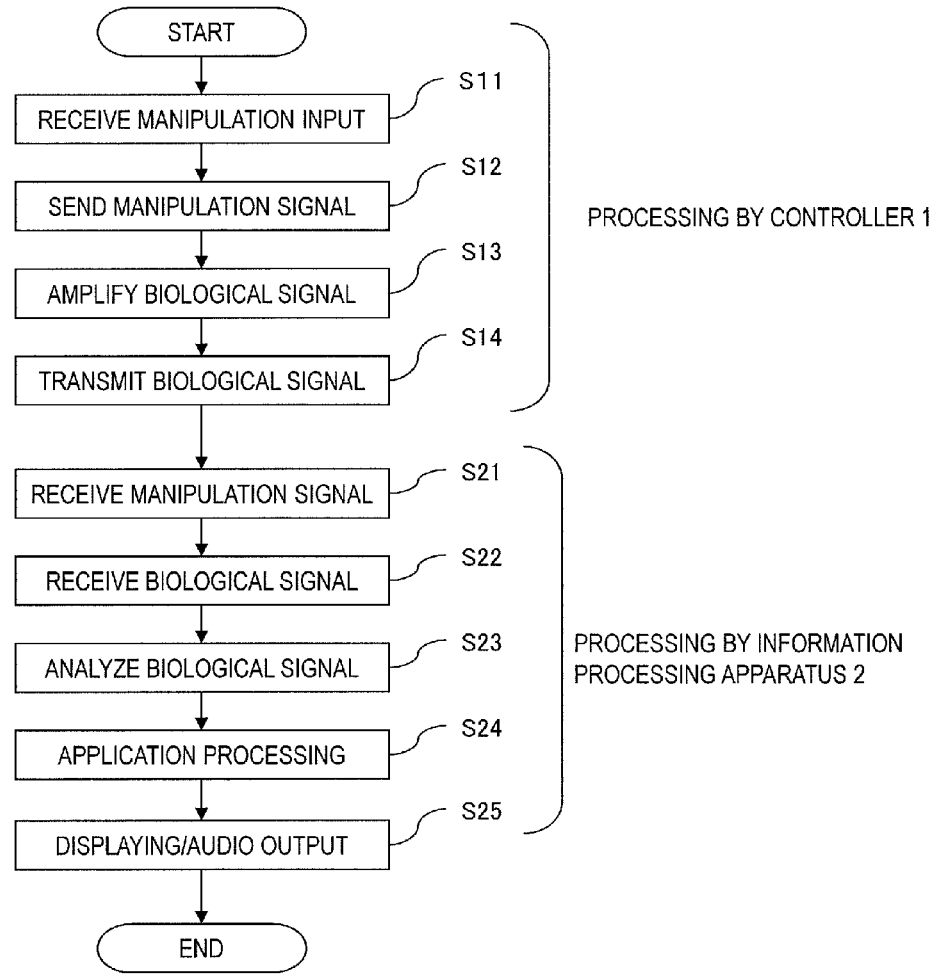
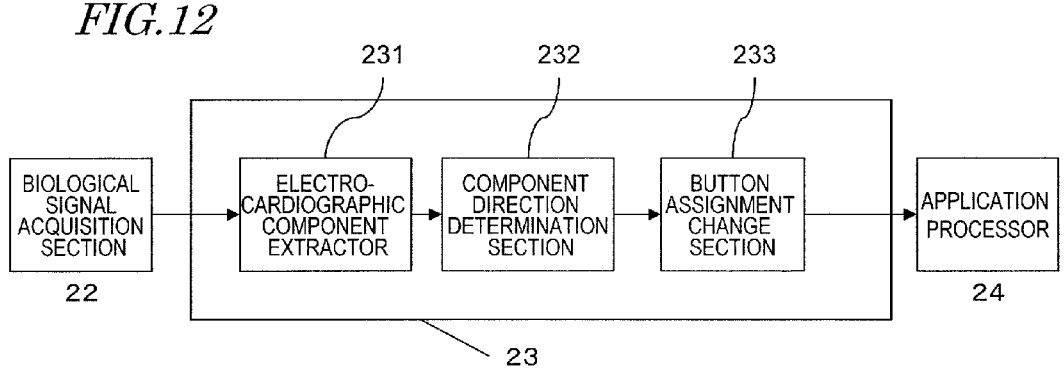

FIG.15
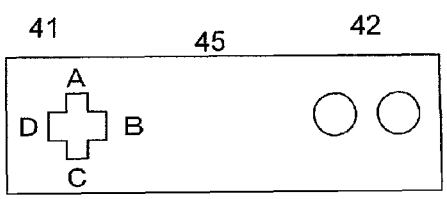
(a)
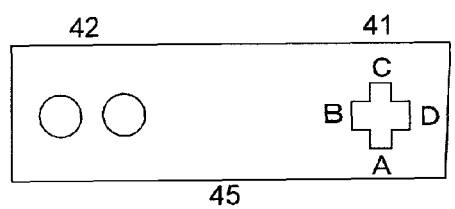
(b)
| CROSS-SHAPED OPERATION BUTTON | FORWARD HOLDING | REVERSE HOLDING |
|---|---|---|
| A | UP | DOWN |
| B | RIGHT | LEFT |
| C | DOWN | UP |
| D | LEFT | RIGHT |
(c)

*FIG.16*
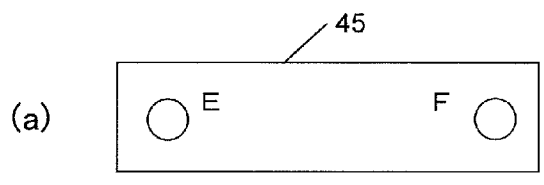
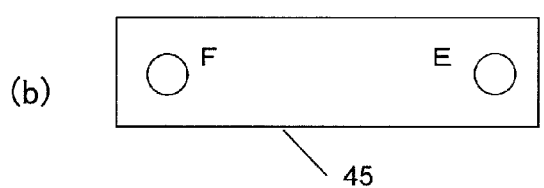
| BUTTON | FORWARD HOLDING | REVERSE HOLDING |
|--------|-----------------|-----------------|
| E | LEFT | RIGHT |
| F | RIGHT | LEFT |
(c)
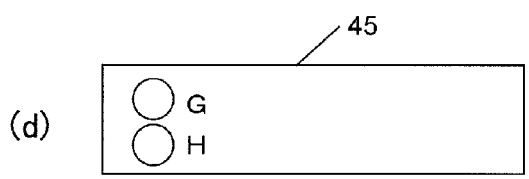
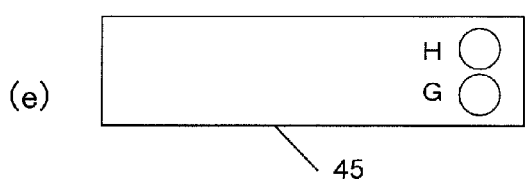
| BUTTON | FORWARD HOLDING | REVERSE HOLDING |
|--------|-----------------|-----------------|
| G | UP | DOWN |
| H | DOWN | UP |
(f)

*FIG.22*

| CURSOR | DURING DETER-MINATION | FINISHED DETERMINATION ||
| --- | --- | --- | --- |
| | | FORWARD HOLDING | REVERSE HOLDING |
| A | UP | UP | "YOU ARE HOLDING IT BACKWARDS" |
| B | RIGHT | RIGHT | "YOU ARE HOLDING IT BACKWARDS" |
| C | DOWN | DOWN | "YOU ARE HOLDING IT BACKWARDS" |
| D | LEFT | LEFT | "YOU ARE HOLDING IT BACKWARDS" |

↑ 281
↑ 282
↑ 283

FIG.23
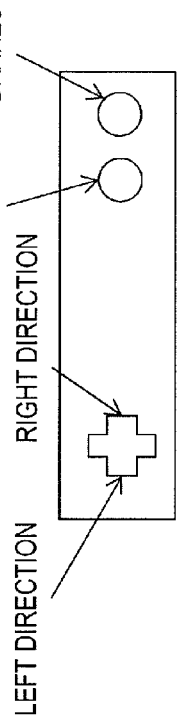
(a)
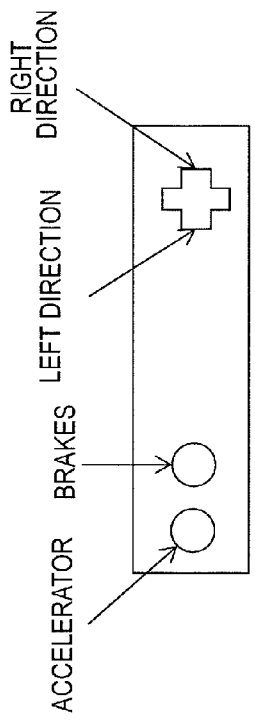
(b-1)
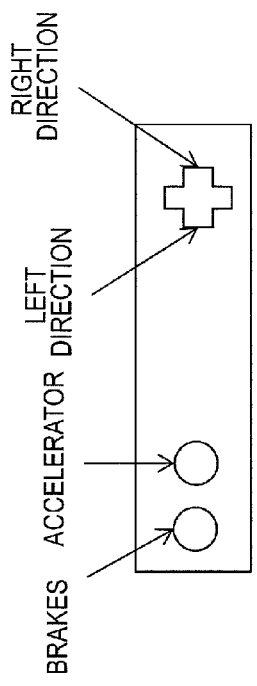
(b-2)
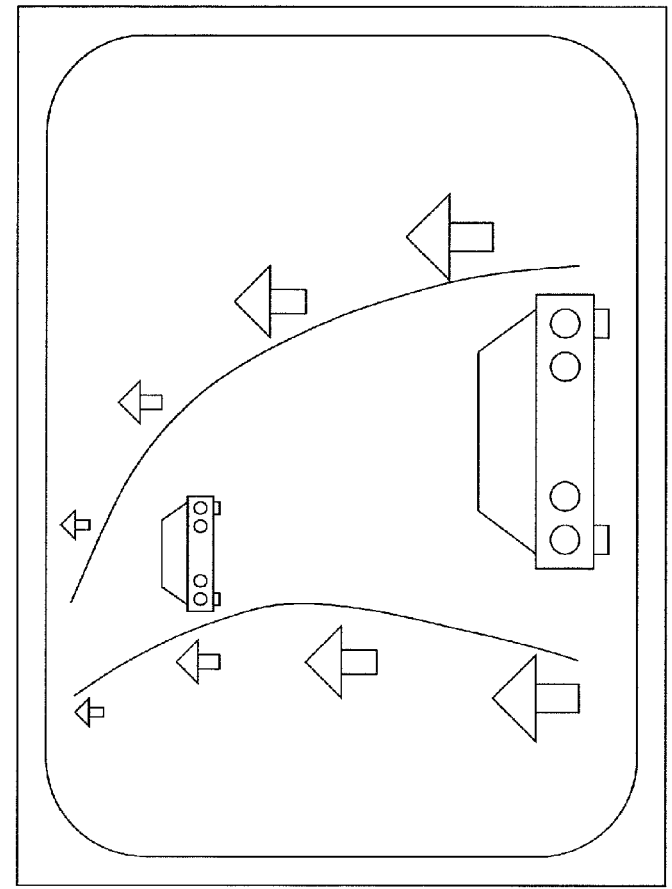

ELECTRONIC DEVICE, INFORMATION PROCESSING APPARATUS, INFORMATION PROCESSING METHOD AND PROGRAM

This is a continuation of International Application No. PCT/JP2013/005347, with an international filing date of Sep. 10, 2013, which claims priority of Japanese Patent Application No. 2012-198235, filed on Sep. 10, 2012, the contents of which are hereby incorporated by reference.

BACKGROUND

1. Technical Field

The present disclosure relates to an electronic device and an information processing system. More specifically, the present disclosure relates to: an information processing system including a controller which combines a means of measuring a bioelectric potential with a means of manipulating an electronic device and an information processing apparatus, such that, when a user manipulates the information processing apparatus, a bioelectric potential signal of the user can be simultaneously measured; and a method and program for achieving the same.

2. Description of the Related Art

In recent years, there has been an increasing need for simplified manipulation in information processing systems such as television sets, personal computers, game machines and smartphones. A manipulation means for such things may be a controller. While facing a display device such as a television set, a user may hold a wireless or wired controller, and, through manipulation of the controller, utilize an application that is executed on the information processing system. For example, in a game machine or the like, while a controller is held in both hands, operation buttons that are assigned to both hands are manipulated by the two hands to play a game. In the case where a means of bioelectric potential measurement is also provided, as is contemplated in the present disclosure, it becomes possible to measure an electrocardiogram or the like, thus enabling monitoring of health states, estimation of psychological states during the game, and so on.

However, while the manipulation scheme of manipulating operation buttons by using both hands may permit versatile control, the need for complex and accurate timing-based manipulation makes the scheme susceptible to influences of handedness, e.g., right-handed or left-handed. When a controller is to be held in both hands, right-handedness is the assumed norm; the problem is that this makes the device difficult for a left-handed person to use in manipulations of making up/down/right/left moves. Also from the standpoint of usability, in the case where it is not clearly known how the controller is to be held, the controller may end up being held in the opposite orientation. Such a situation needs to be overcome by an arrangement such that manipulation is equally permitted in the opposite orientation, or a notice to the user that the manner of holding is wrong when the controller is indeed held in the opposite orientation.

Thus, in a scenario where a controller is to be held in both hands, a plurality of manners of holding are conceivable. An ability to detect how it is held would make for an improved operability.

In conventional means of bioelectric potential measurement, it is required that electrodes for potential measurement be accurately mounted, and a method for determining their accurate mounting have been proposed. For example, Japanese Laid-Open Patent Publication Nos. 2002-233513 and 2009-261723 disclose techniques of issuing a notification of wrong mounting based on the waveform and amplitude of a measured bioelectric potential.

SUMMARY

The prior art technique needs further improvement in view of detection of a manner of holding a controller, as discussed above, based on a bioelectric potential signal.

One non-limiting, and exemplary embodiment provides an electronic device having a function of measuring a bioelectric potential signal, where a manner of holding is detected by analyzing a measured bioelectric potential signal, and a manipulation method which is in accordance with the manner of holding is provided.

In one general aspect, an electronic device according to the present disclosure is in a housing to be gripped by a right hand and a left hand of a user, the electronic device having a plurality of manipulable portions, comprising: a first electrode and a second electrode placed at positions which come in contact with the right hand and left hand of the user gripping the housing; an extractor for extracting an electrocardiographic component of the user from a potential difference between the first electrode and the second electrode; a determination section for determining whether the electrocardiographic component extracted by the extractor is in a positive direction or a negative direction by referring to a prestored criterion concerning electrocardiographic component potential; and a change section for, in accordance with a result of determination by the determination section, changing assignment between each of the plurality of manipulable portions and a manipulation signal generated in response to a manipulation, the change section assigning each of the plurality of manipulable portions to a respective manipulation signal under a first relationship when the result of determination indicates the positive direction, and assigning each of the plurality of manipulable portions to a respective manipulation signal under a second relationship when the result of determination indicates the negative direction, the second relationship being different from the first relationship.

According to the above aspect, even when a user holds a controller in an arbitrary manner to his or her own liking, an electronic device according to one implementation of the present invention detects the manner of holding through analysis of a bioelectric potential signal, and provides a manipulation method which is in accordance with the manner of holding, thereby providing an improved operability for the user.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 1 is a diagram showing a manner in which an information processing system 100 may be used.

FIGS. 4A and 4B are diagrams showing examples of electrode positions in the case where electrodes are disposed on the upper side face.

Portions (a) to (d) of FIG. 5 shows examples of electrode shapes and numbers of electrodes.

FIGS. 6A to 6C are diagrams showing other examples of electrode shapes.

FIG. 7 is a diagram showing a system construction for the information processing system 100.

Figure 8:
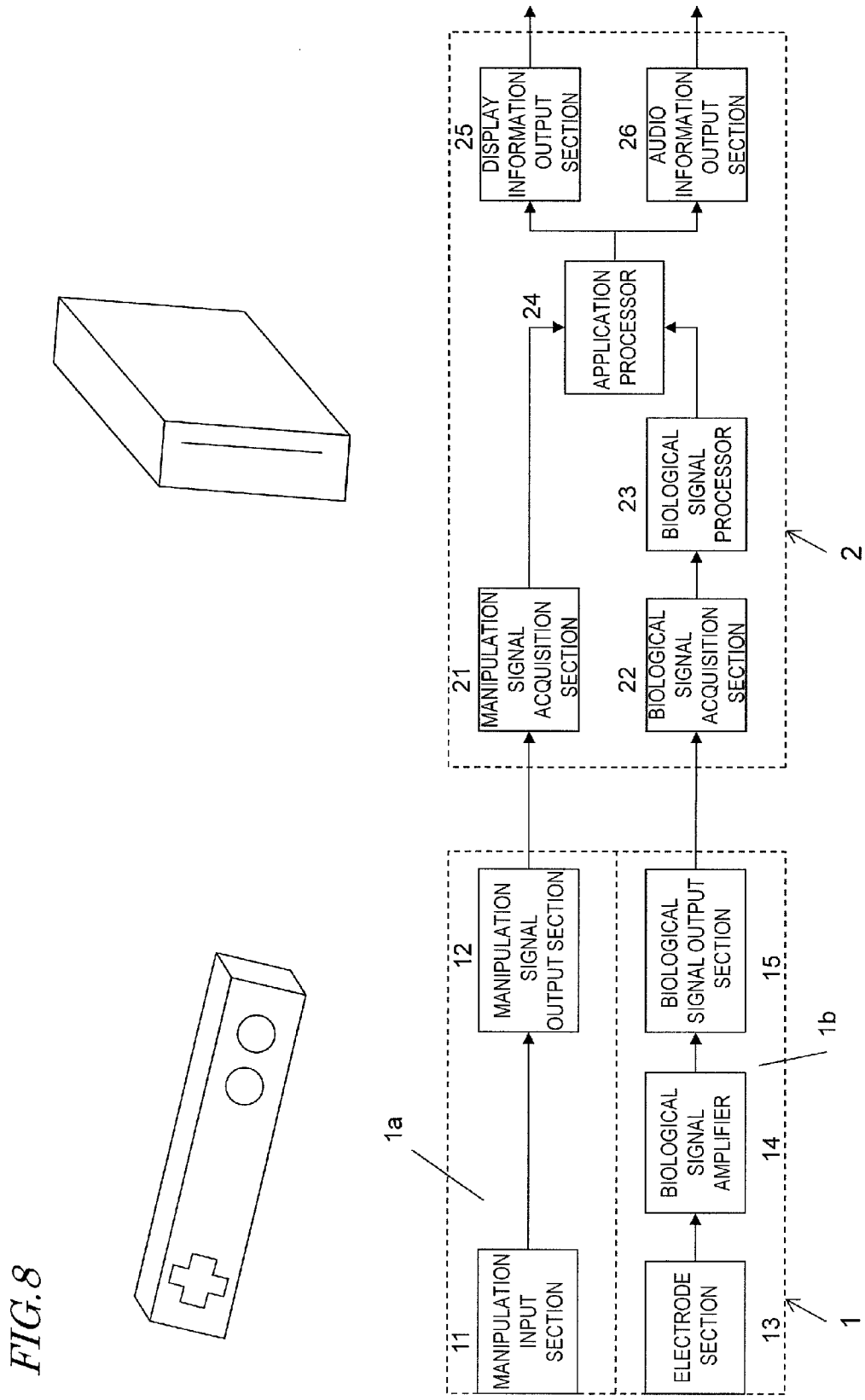

FIG. 8 is a diagram showing the construction of a controller 1 and an information processing apparatus 2 of the information processing system 100.

Figure 9:
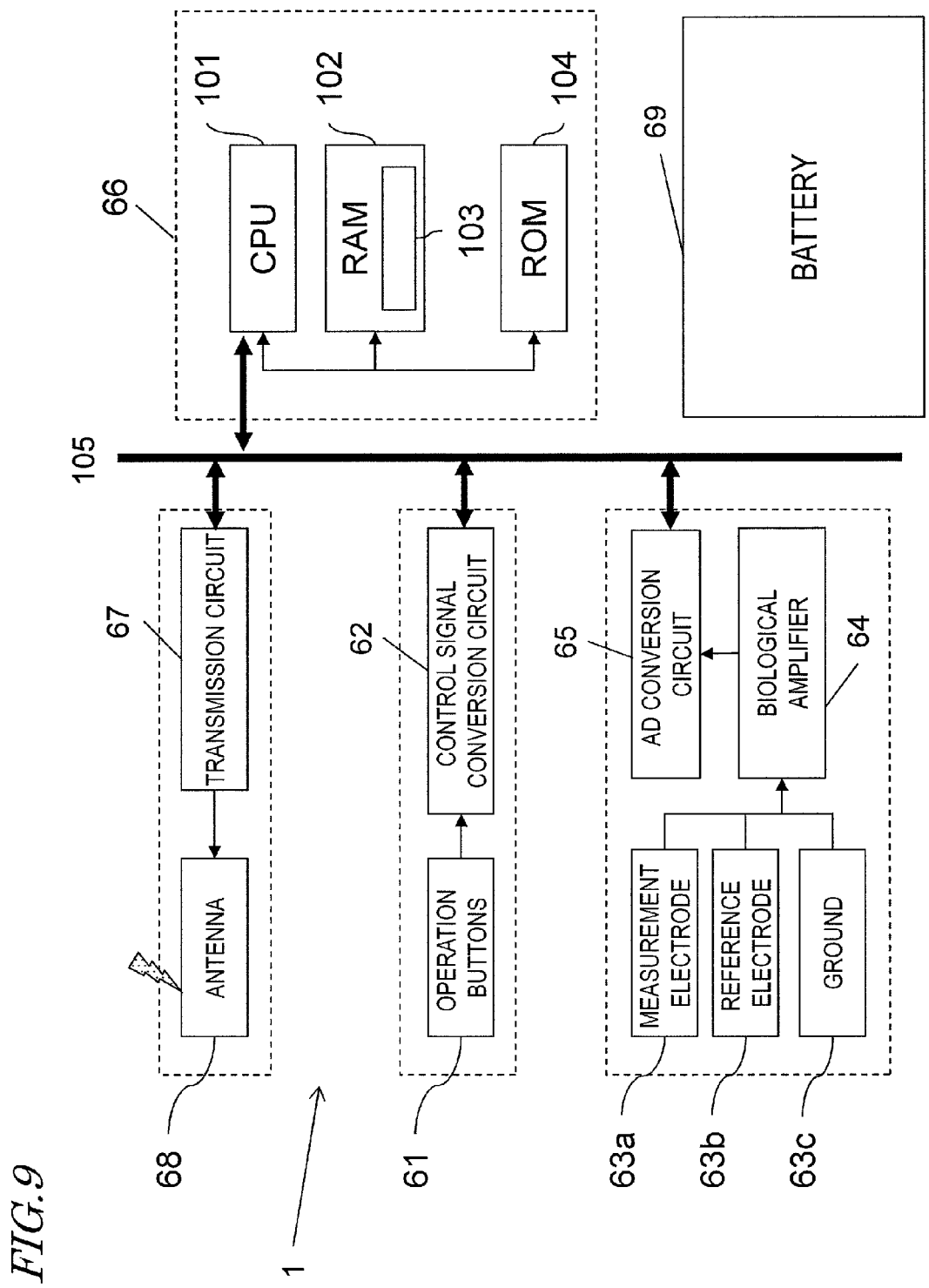

FIG. 9 is a diagram showing the hardware construction of a controller.

Figure 10:
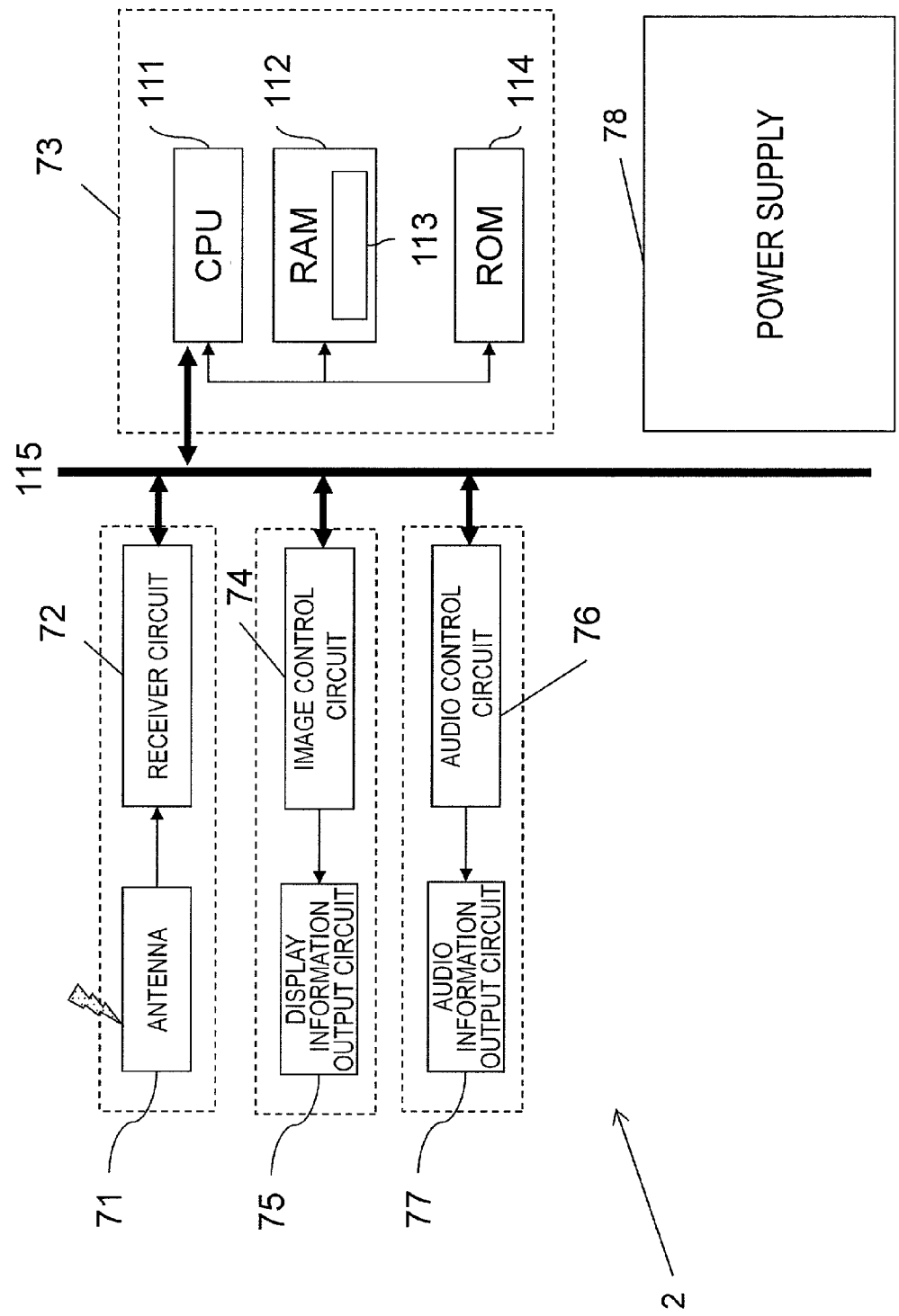

FIG. 10 is a diagram showing the hardware construction of the information processing apparatus 2 of the information processing system 100.

FIG. 11 is a flowchart of fundamental processes by the information processing system 100.

FIG. 12 is a diagram showing the construction of a biological signal processor 23 in Embodiment 1.

Figure 13:
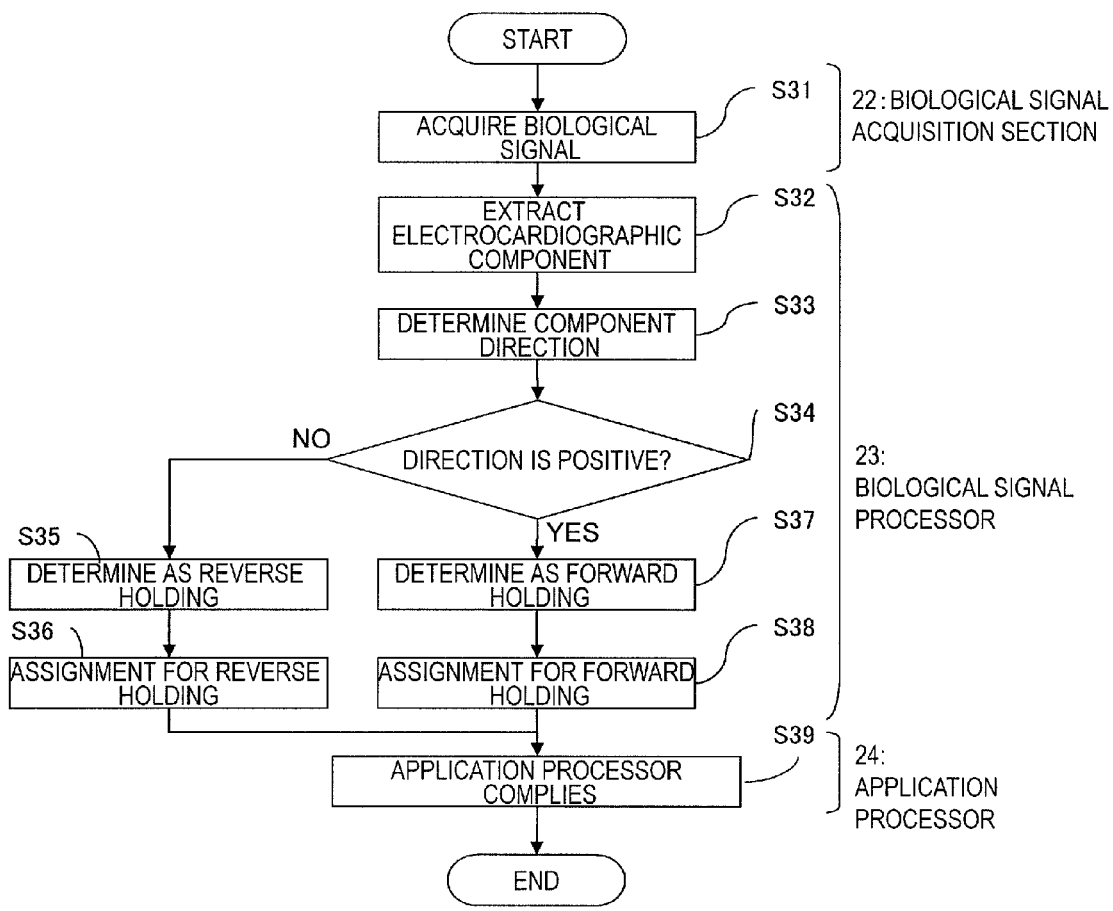

FIG. 13 is a flowchart showing a manner-of-holding determination, mainly concerning the biological signal processor 23.

Figure 14:
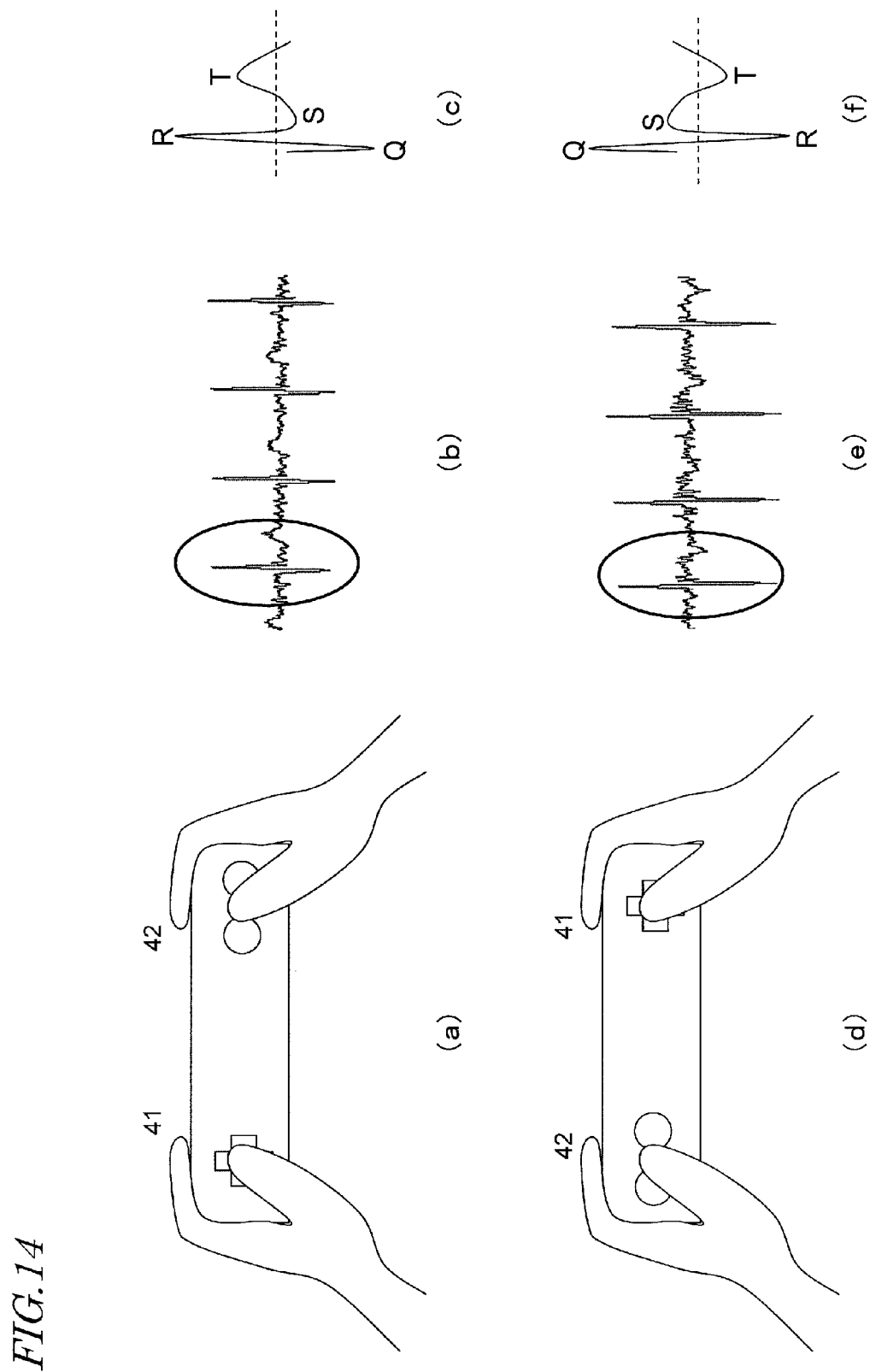

Portions (a) to (c) of FIG. 14 are diagrams showing forward holding and examples of corresponding bioelectric potential signals; and portions (d) to (f) of FIG. 14 are diagrams showing reverse holding and examples of corresponding bioelectric potential signals.

Portions (a) to (c) of FIG. 15 are diagrams showing examples of assignment of operation buttons to control signals, as adapted to different manners of holding.

Portions (a) to (f) of FIG. 16 are diagrams showing other examples of button assignment.

Figure 17A:
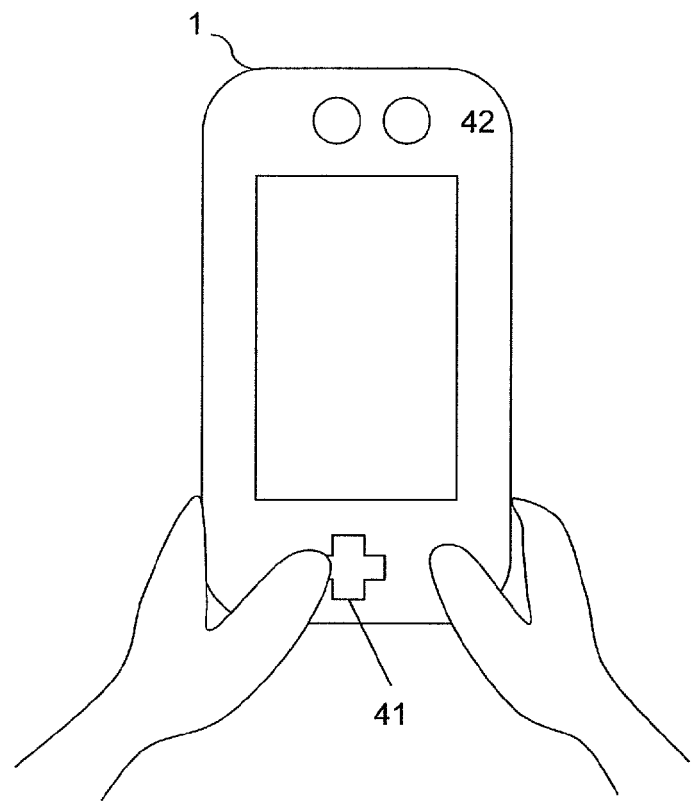

FIG. 17A is a diagram showing an instance of portrait orientation of a pad-type controller.

Figure 17B:
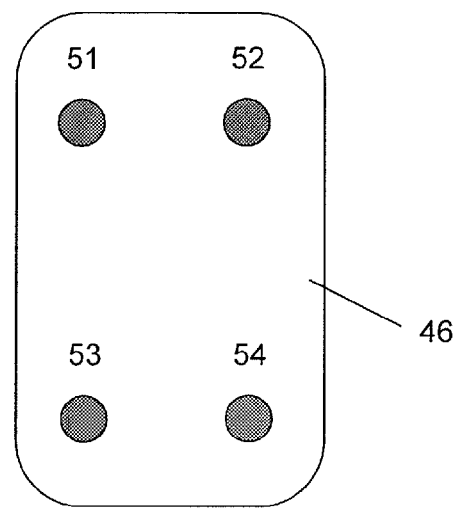

FIG. 17B is a diagram showing a rear face 46 of the pad-type controller 1 shown in FIG. 17A.

Figure 17C:
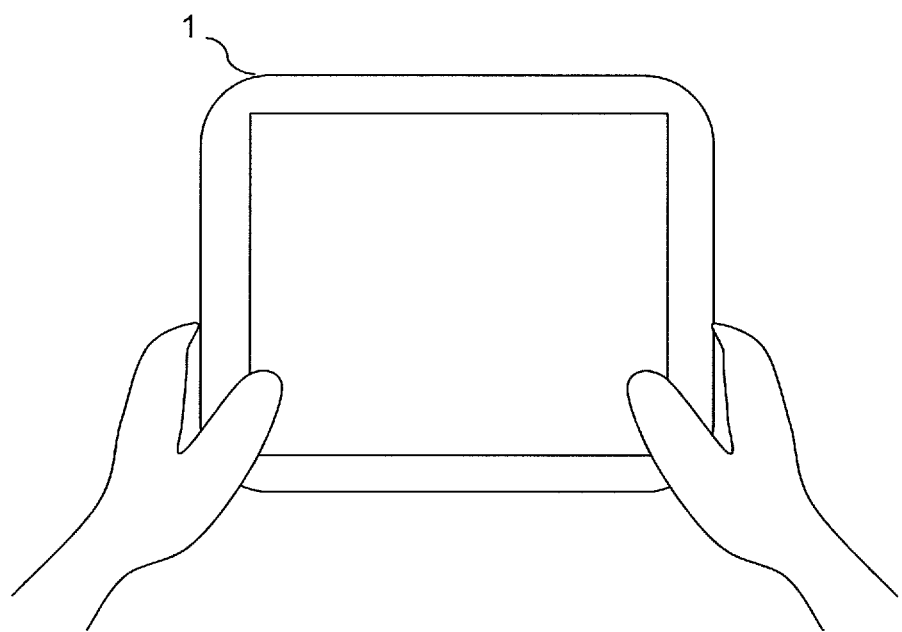

FIG. 17C is a diagram showing an instance of landscape orientation of a tablet-type controller 1.

Figure 17D:
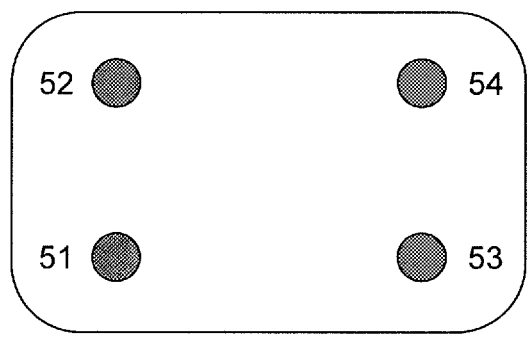

FIG. 17D is a diagram showing a rear face 46 of the tablet-type controller 1 shown in FIG. 17C.

Figure 17E:
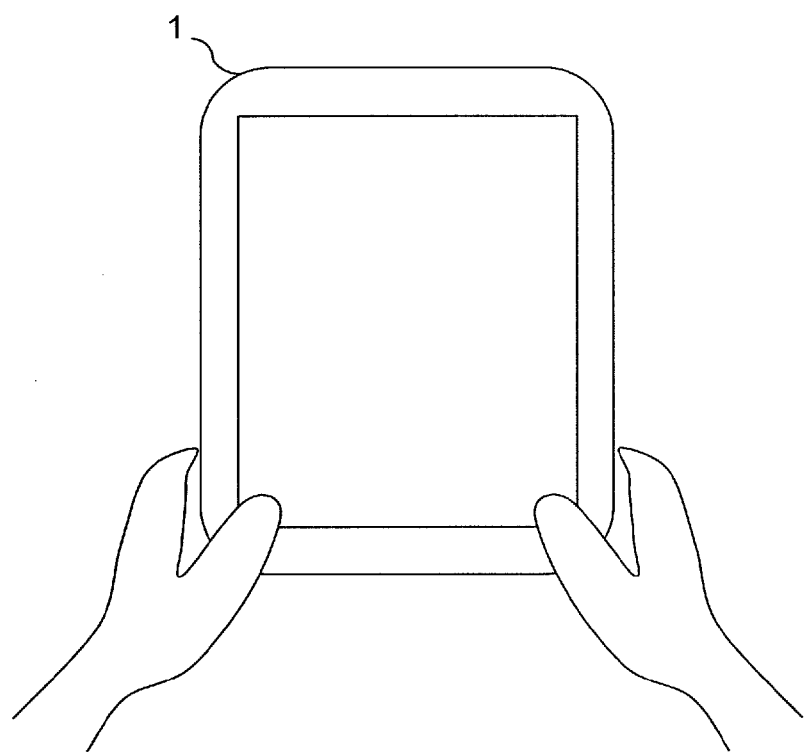

FIG. 17E is a diagram showing an instance of portrait orientation of the tablet-type controller 1.

Figure 17F:
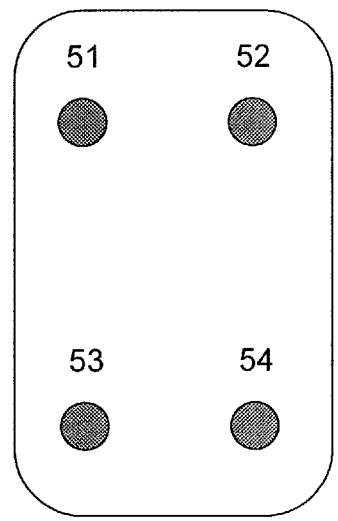

FIG. 17F is a diagram showing a rear face 46 of the tablet-type controller 1 shown in FIG. 17E.

Figure 18:
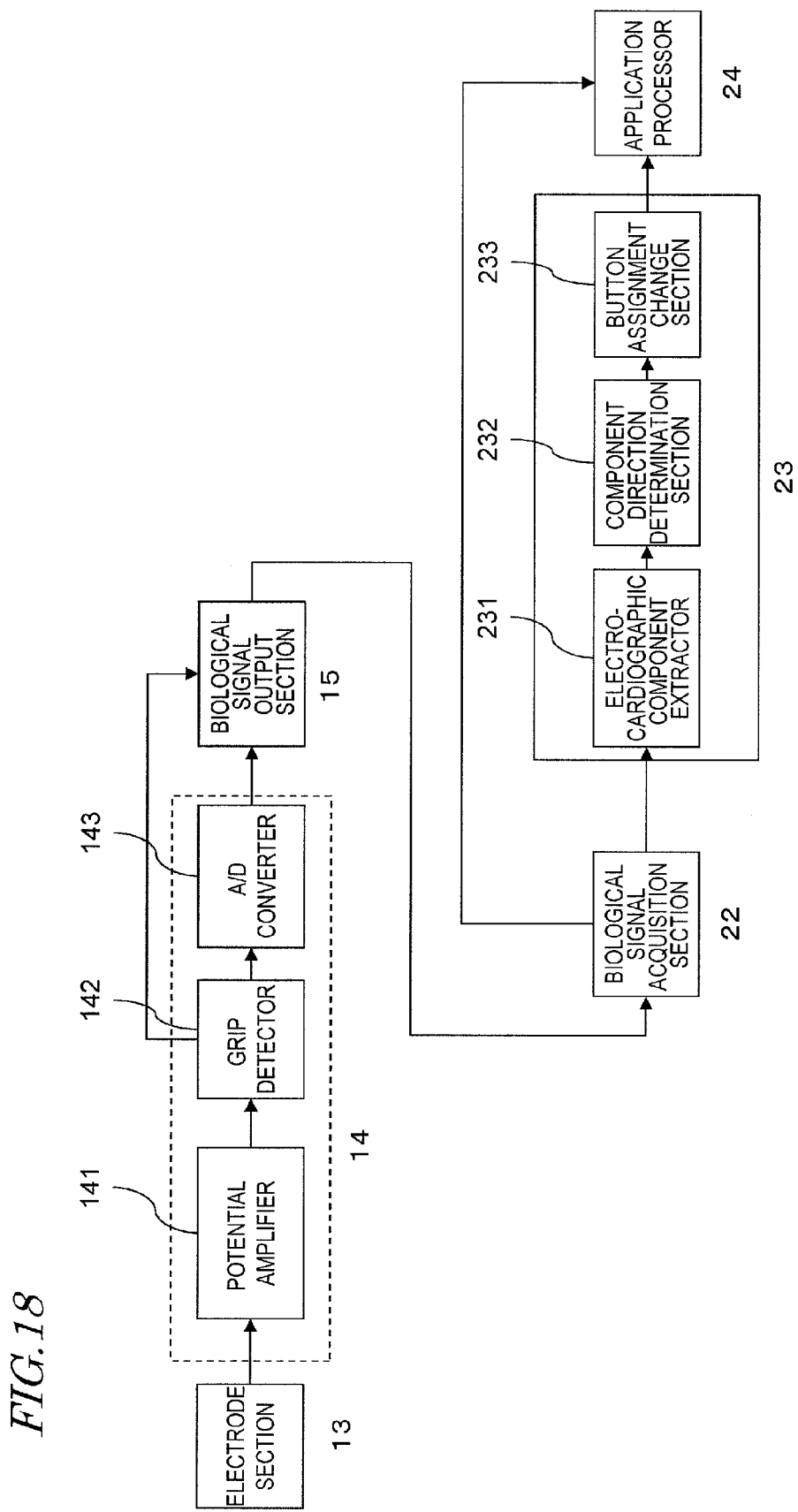

FIG. 18 is a diagram showing the construction of a bioelectric potential amplifier and a biological signal processor in Embodiment 2.

Figure 19:
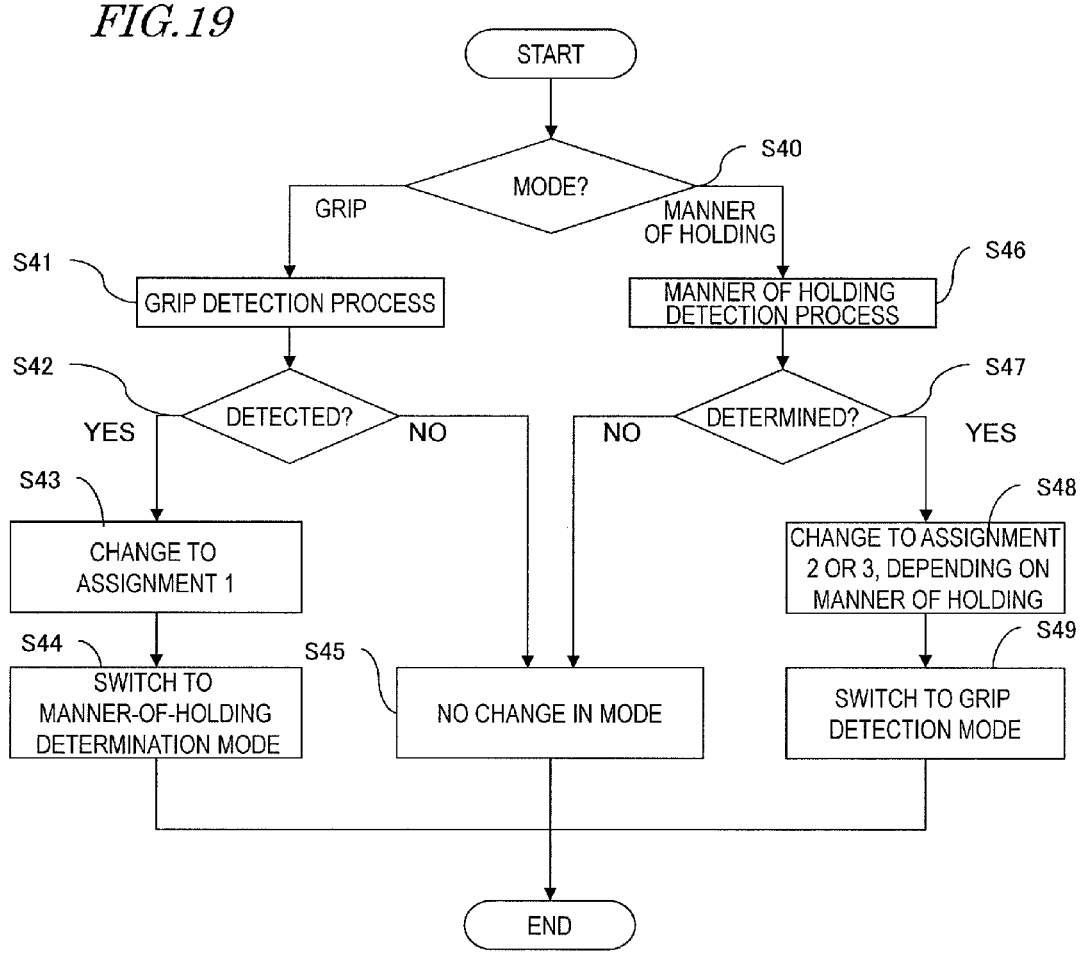

FIG. 19 is a flowchart showing a grip and manner-of-holding determination processes for a controller.

Figure 20:
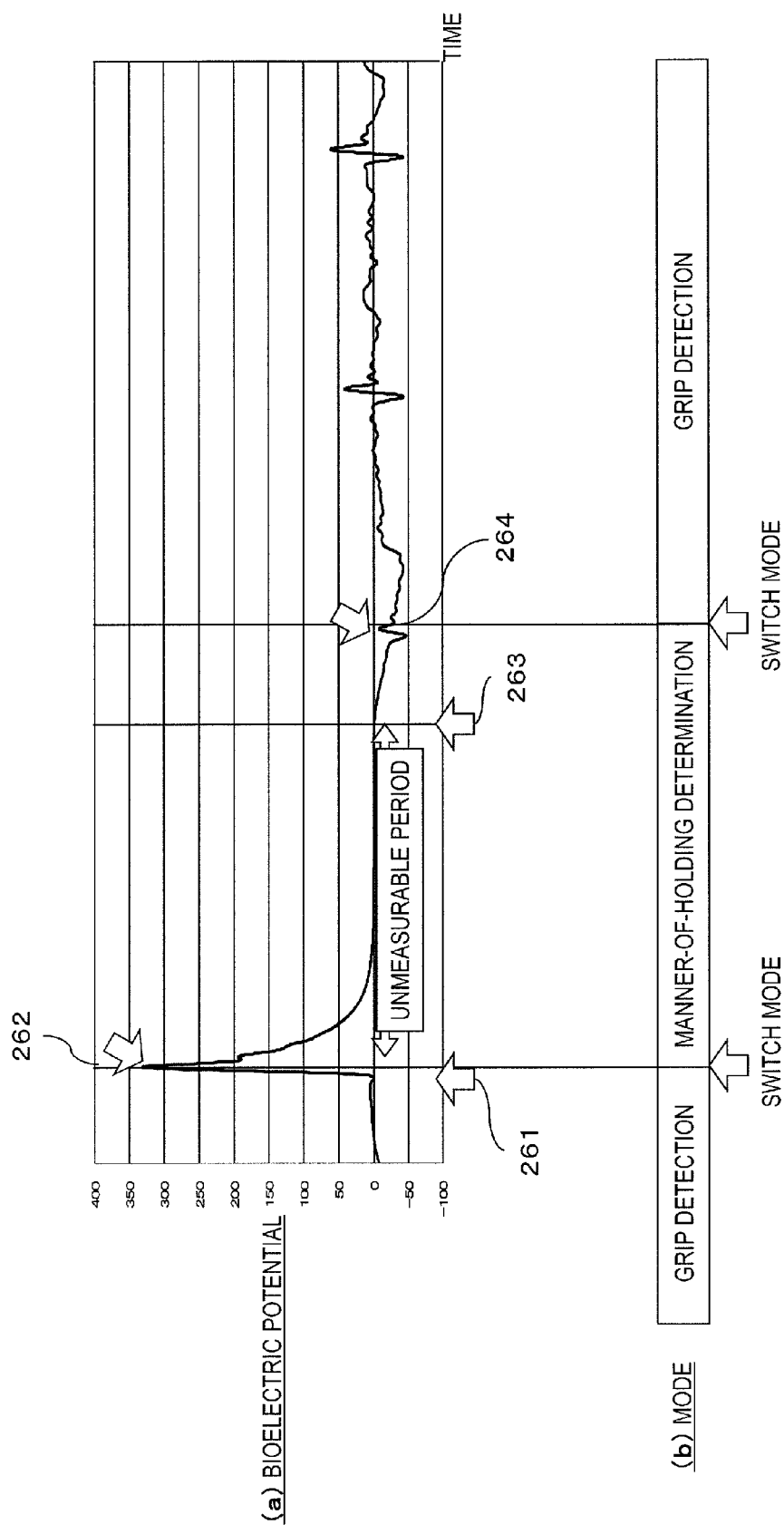

Portions (a) and (b) of FIG. 20 are diagrams showing changes in a bioelectric potential signal after a controller is gripped.

Figure 21:
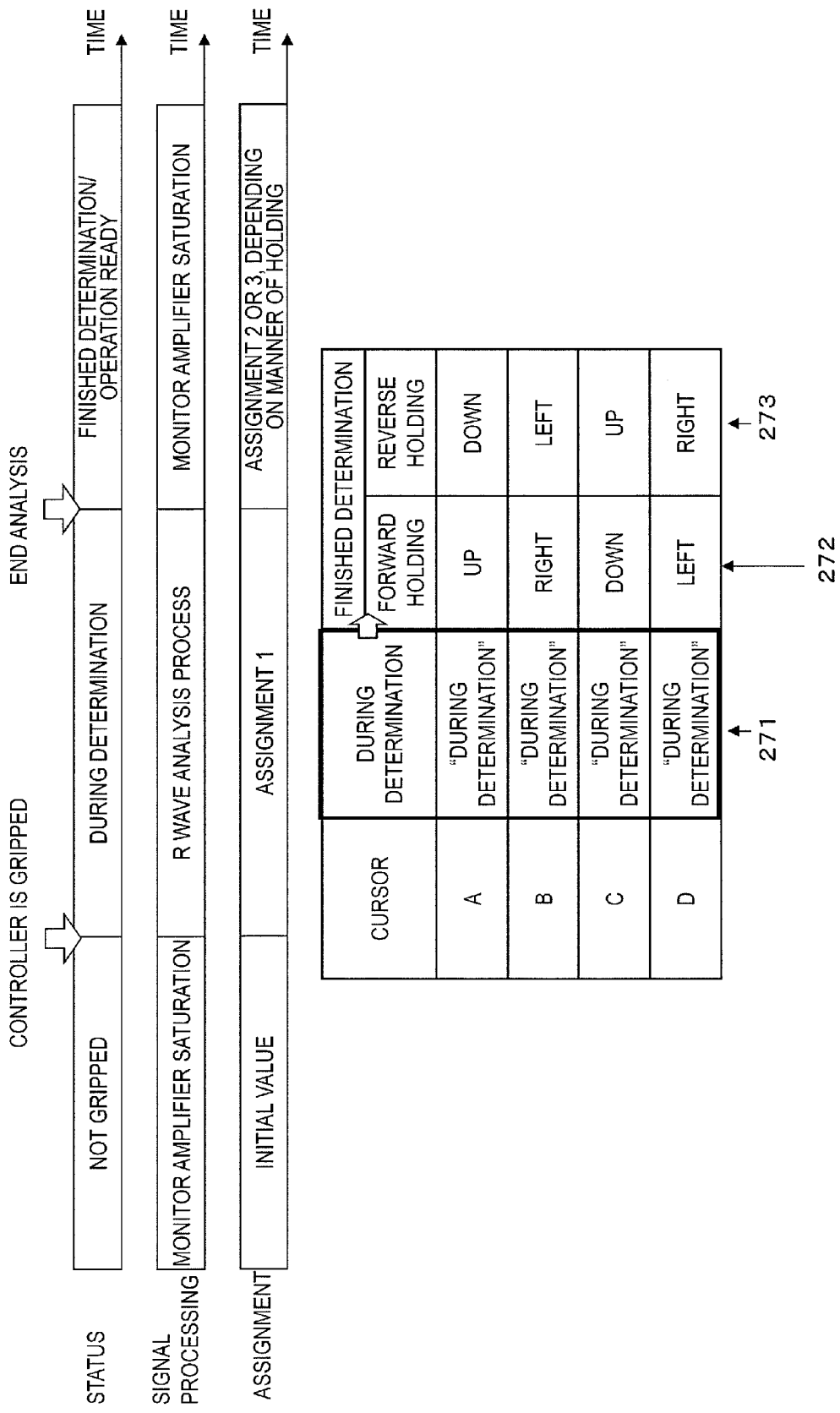

FIG. 21 is a diagram showing gripped/ungripped states and assignment of operation buttons to control signals adapted to the manner of holding.

FIG. 22 is a diagram showing examples of assignment in the case of a right-handed only application.

Portions (a), (b-1) and (b-2) of FIG. 23 are diagrams showing examples of assignment for a controller of a racing game.

Figure 24A:
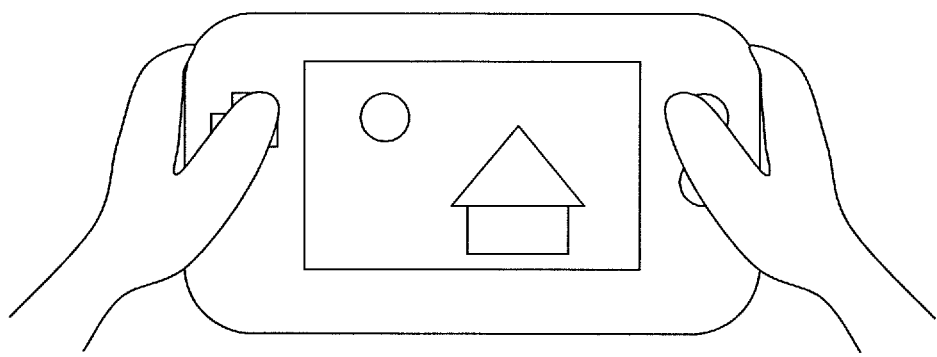
Figure 24B:
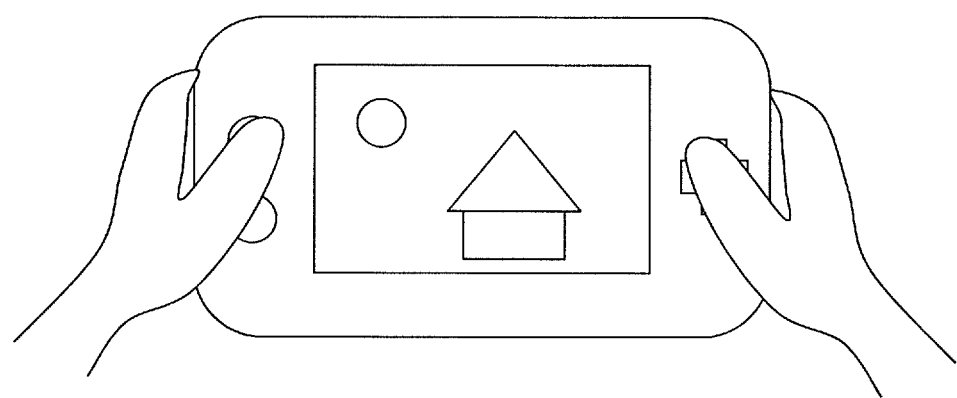

FIGS. 24A and 24B are diagrams showing reversal of an image on a controller having a display screen.

Figure 25:
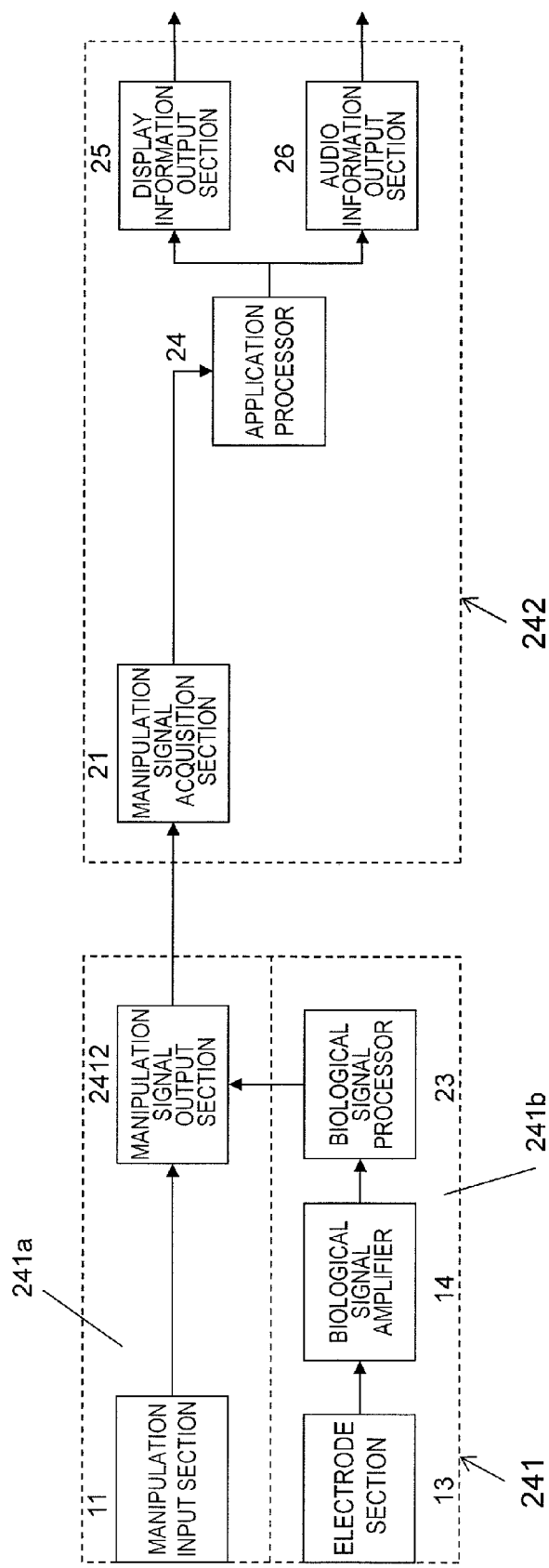

FIG. 25 is a diagram showing a variant of the construction of FIG. 8.

Figure 26:
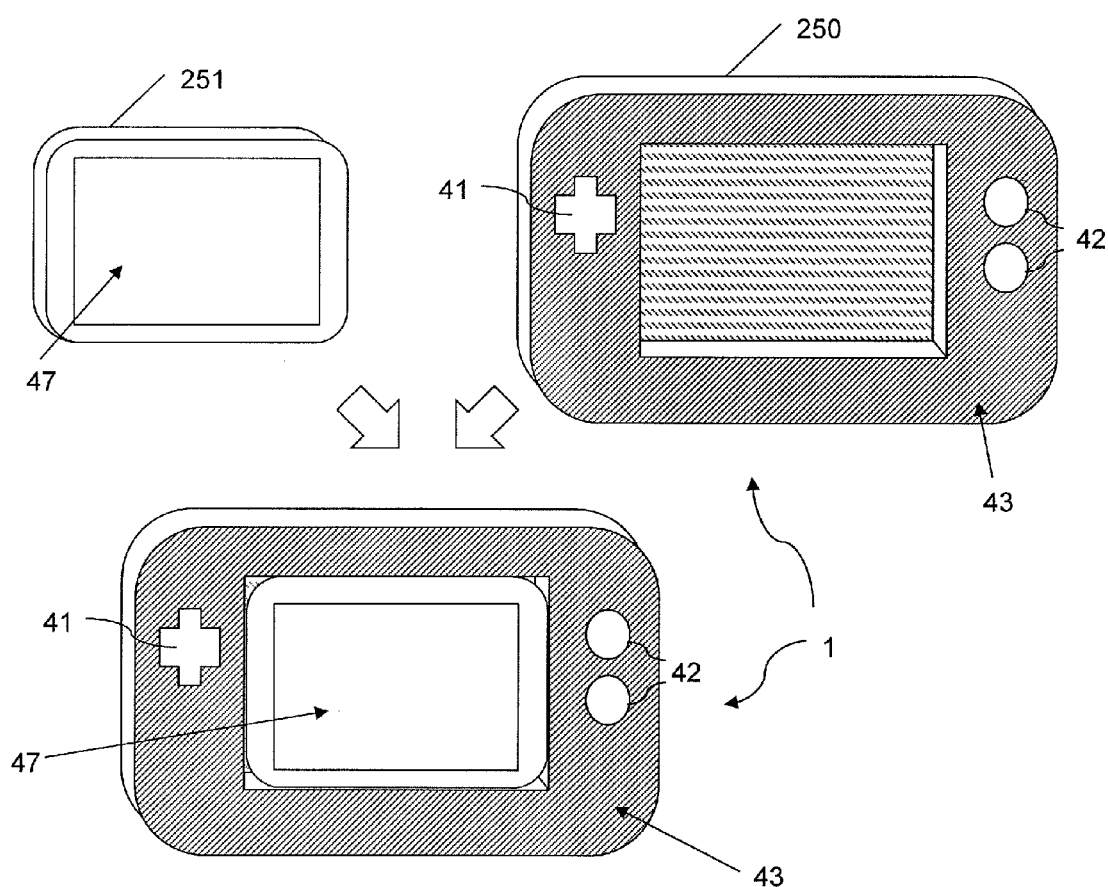

FIG. 26 is a diagram showing an example of a controller 1 which combines an attachment 250 and a smartphone 251.

Figure 27:
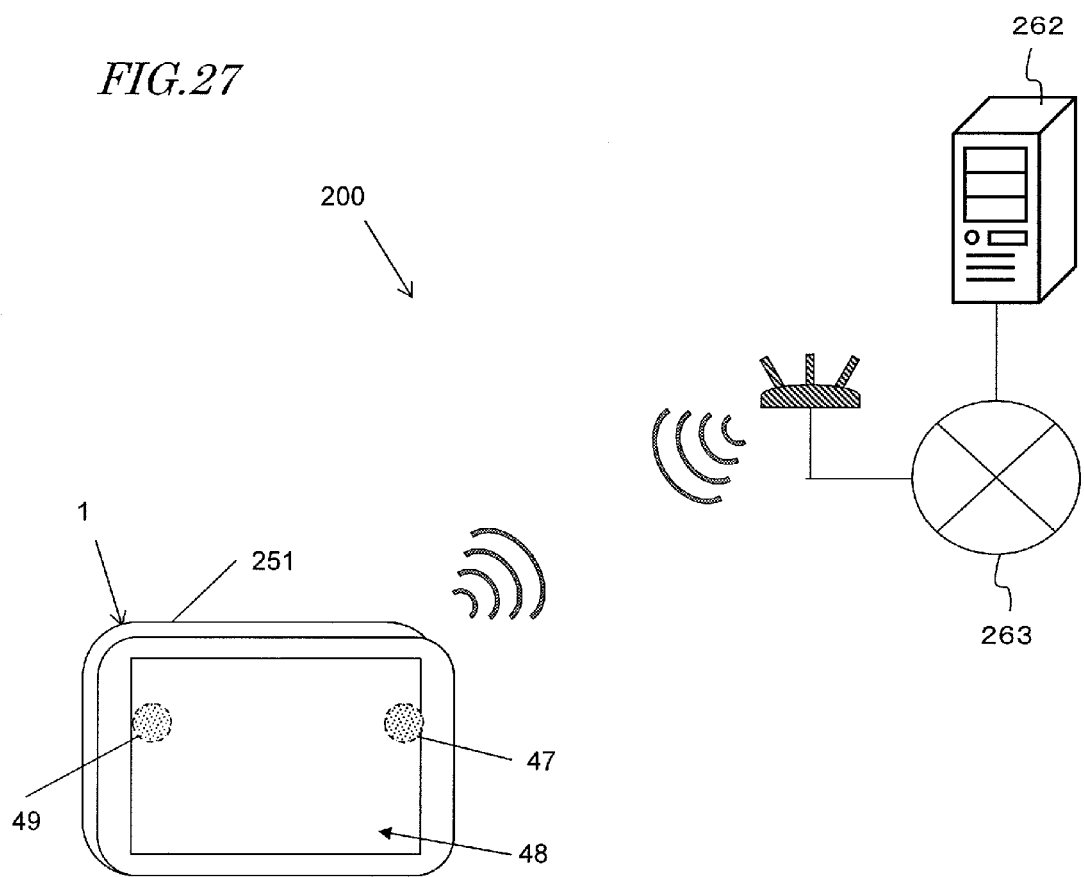

FIG. 27 is a diagram showing the construction of an information processing system 200, which is a variant of the information processing system according to Embodiment 1 or 2.

DETAILED DESCRIPTION

The findings which provided the basis for the present invention are as follows.

Conventional techniques have not necessarily been easy to handle for users, because they require accurate mounting of electrodes for potential measurement.

One implementation of the present invention is as follows, in outline.

An electronic device as one implementation of the present invention is in a housing to be gripped by a right hand and a left hand of a user, the electronic device having a plurality of manipulable portions, comprising: a first electrode and a second electrode placed at positions which come in contact with the right hand and left hand of the user gripping the housing; an extractor for extracting an electrocardiographic component of the user from a potential difference between the first electrode and the second electrode; a determination section for determining whether the electrocardiographic component extracted by the extractor is in a positive direction or a negative direction by referring to a prestored criterion concerning electrocardiographic component potential; and a change section for, in accordance with a result of determination by the determination section, changing assignment between each of the plurality of manipulable portions and a manipulation signal generated in response to a manipulation, the change section assigning each of the plurality of manipulable portions to a respective manipulation signal under a first relationship when the result of determination indicates the positive direction, and assigning each of the plurality of manipulable portions to a respective manipulation signal under a second relationship when the result of determination indicates the negative direction, the second relationship being different from the first relationship.

In one embodiment, the extractor extracts an R wave as the electrocardiographic component. In one embodiment, the determination section further extracts a Q wave as the electrocardiographic component, and distinguishes between the positive direction and the negative direction based on a direction of change of the QR component.

In one embodiment, the extractor extracts a T wave as the electrocardiographic component; and the determination section distinguishes between the positive direction and the negative direction based on whether the T wave has an upward peak or a downward peak.

One embodiment comprises a moving direction designator button for a cursor, wherein the change section changes assignment between directions on the moving direction designator button and manipulation signals.

In one embodiment, the moving direction designator button is a button capable of moving the cursor in four directions of up, down, right, and left; and the change section assigns a first manipulation signal to an upward manipulation and assigns a second manipulation signal to a downward manipulation, under the first relationship, or assigns the second manipulation signal to an upward manipulation and assigns the first manipulation signal to a downward manipulation under the second relationship.

In one embodiment, the moving direction designator button is a button capable of moving the cursor in four directions of up, down, right, and left; and the change section assigns a third manipulation signal to a leftward manipulation and assigns a fourth manipulation signal to a rightward manipulation under the first relationship, or assigns the fourth manipulation signal to a leftward manipulation and assigns the third manipulation signal to a rightward manipulation under the second relationship.

One embodiment further comprises a grip detector for detecting a timing at which the user grips the housing with both hands, the timing being detected as a timing at which the potential difference between the first electrode and the second electrode becomes equal to or greater than a predetermined level.

In one embodiment, the extractor and the determination section respectively begin processing at the timing.

In one embodiment, after processing by the determination section is begun and until a result of determination is obtained, the change section changes the assignment between each of the plurality of manipulable portions and a manipulation signal to that of a predetermined relationship; and after the result of determination is obtained, the change section changes the assignment between each of the plurality of manipulable portions and a manipulation signal to that of a relationship conforming to the result of determination.

In one embodiment, the change section receives information of application software which is currently under execution, and accordingly changes the assignment.

One embodiment further comprises a manipulation signal output section for outputting to an external information processing apparatus a manipulation signal in response to a manipulation of one of the plurality of manipulable portions.

An information processing apparatus as one implementation of the present invention comprises: a manipulation signal acquisition section for receiving a manipulation signal from an electronic device having a plurality of manipulable portions; a biological signal acquisition section for acquiring a biological signal of the user sent from the electronic device, the biological signal being a signal derived from a potential difference between a first electrode and a second electrode placed at positions which come in contact with a right hand and a left hand of the user gripping a housing of the electronic device; an extractor for extracting an electrocardiographic component of the user from the acquired biological signal; a determination section for determining whether the extracted electrocardiographic component is in a positive direction or a negative direction by referring to a prestored criterion concerning electrocardiographic component potential; and a change section for, in accordance with a result of determination by the determination section, changing assignment between each of the plurality of manipulable portions and a manipulation signal generated in response to a manipulation, the change section assigning each of the plurality of manipulable portions to a respective manipulation signal under a first relationship when the result of determination indicates the positive direction, and assigning each of the plurality of manipulable portions to a respective manipulation signal under a second relationship when the result of determination indicates the negative direction, the second relationship being different from the first relationship.

An information processing method as one implementation of the present invention is an information processing method using an electronic device, wherein the electronic device is in a housing to be gripped by a right hand and a left hand of a user, the electronic device having a plurality of manipulable portions and a first electrode and a second electrode placed at positions which come in contact with the right hand and left hand of the user gripping the housing, the method comprising the steps of: extracting an electrocardiographic component of the user from a potential difference between the first electrode and the second electrode; determining whether the electrocardiographic component extracted by the extracting step is in a positive direction or a negative direction by referring to a prestored criterion concerning electrocardiographic component potential; and in accordance with a result of determination by the determining step, changing assignment between each of the plurality of manipulable portions and a manipulation signal generated in response to a manipulation, so that each of the plurality of manipulable portions is assigned to a respective manipulation signal under a first relationship when the result of determination indicates the positive direction, and that each of the plurality of manipulable portions is assigned to a respective manipulation signal under a second relationship when the result of determination indicates the negative direction, the second relationship being different from the first relationship.

A computer program as one implementation of the present invention is a computer program to be executed by a computer mounted in an electronic device, wherein the electronic device is in a housing to be gripped by a right hand and a left hand of a user, the electronic device having a plurality of manipulable portions and a first electrode and a second electrode placed at positions which come in contact with the right hand and left hand of the user gripping the housing, the computer program causing the computer to execute the steps of: extracting an electrocardiographic component of the user from a potential difference between the first electrode and the second electrode; determining whether the electrocardiographic component extracted by the extracting step is in a positive direction or a negative direction by referring to a prestored criterion concerning electrocardiographic component potential; and in accordance with a result of determination by the determining step, changing assignment between each of the plurality of manipulable portions and a manipulation signal generated in response to a manipulation, so that each of the plurality of manipulable portions is assigned to a respective manipulation signal under a first relationship when the result of determination indicates the positive direction, and that each of the plurality of manipulable portions is assigned to a respective manipulation signal under a second relationship when the result of determination indicates the negative direction, the second relationship being different from the first relationship.

Hereinafter, with reference to the attached drawings, embodiments of the "information processing system" according to one implementation of the present disclosure will be described.

(Description of a System Including an Information Processing Apparatus)

FIG. 1 shows a manner in which an information processing system 100 may be used. The information processing system 100 shown in FIG. 1 includes a controller 1, an information processing apparatus 2, and a display device 3. The controller 1, the information processing apparatus 2, and the display device 3 are interconnected in a wired or wireless manner to enable exchange of information.

The controller 1 includes input means for allowing a user to input manipulation information, with which the user manipulates the information processing apparatus 2. A manipulation for realizing a desired process may be input to the input means.

The information processing apparatus 2 receives a manipulation input from the controller 1, and performs a predetermined process. In the present specification, the "predetermined process" collectively refers to any application to be executed on a computer for household use, e.g., games, health management, learning, and so on.

The display device 3 displays a processing result by the information processing apparatus 2. The display device displays image information, or presents audio information.

(Controller Shape)

Figure 2A:
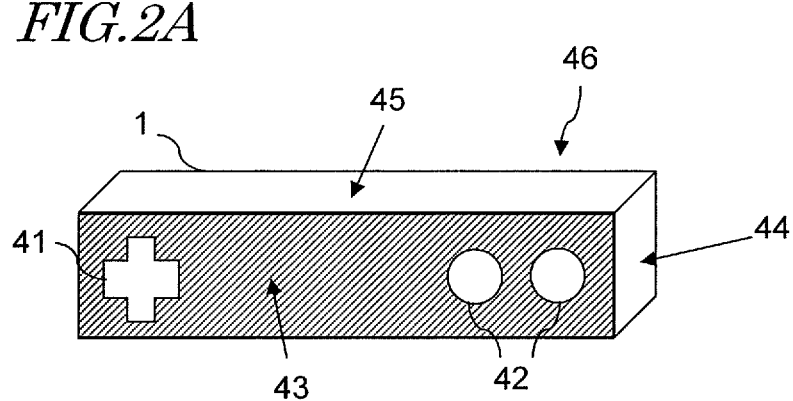
FIGS. 2A and 2B are diagrams showing examples of controller shapes and the names of faces.
Figure 2B:
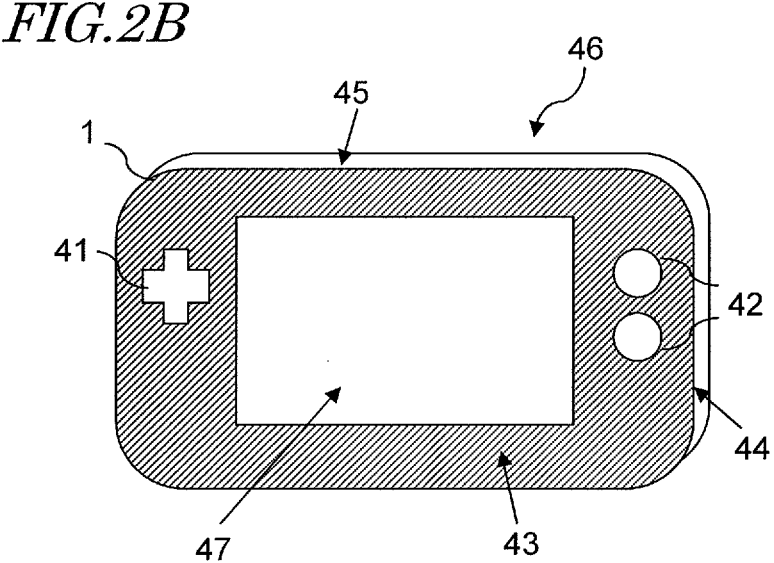

FIGS. 2A and 2B show example shapes of the controller 1. For example, a user may hold the controller 1 in both hands to manipulate it. Examples of the appearance of the controller 1 are the stick type as shown in FIG. 2A, and the pad type as shown in FIG. 2B.

A stick-type controller 1 shown in FIG. 2A has a stick shape of a laterally elongated bar. The user holds it at both ends, so as to manipulate an operation button 41 with the left thumb, and operation buttons 42 with the right thumb. In the illustrated example, the operation button 41 is of a type which enables input in the up/down/right/left directions, and the operation buttons 42 are two buttons for providing twofold control.

The pad-type controller 1 shown in FIG. 2B has a plate-like pad shape. The user holds it at both sides, so as to manipulate an operation button 41 with the left thumb, and operation buttons 42 with the right thumb. A display screen 47 is provided in the central portion of the pad, where the state of manipulation and/or processing results of an application can be displayed.

Note that, as will be described later, further diversified controllers 1 may also be possible, including a tablet-type controller (FIG. 17B), a controller in which a smartphone is incorporated into an attachment (FIG. 26), and a controller which combines a smartphone and electrodes (variant of FIG. 26). Any such controller 1 will be collectively referred to as an "electronic device" in the present specification.

(Definition of Faces)

With reference to FIGS. 2A and 2B, the names of faces used in the present specification will be defined.

The controller 1 has a manipulation surface 43, a left side face (not shown), a right side face 44, an upper side face 45, a lower side face (not shown), and a rear face 46.

The manipulation surface 43 shown in FIGS. 2A and 2B is a face on which the operation button 41 and the operation buttons 42 are placed.

As one faces the manipulation surface 43 as shown in the figure, the side faces which appear to the right/left/above/below of the manipulation surface 43 are, respectively, the right side face 44, the left side face (not shown), the upper side face 45, and the lower side face (not shown). The opposite face from the manipulation surface 43 is the rear face 46.

The manipulation surface can be similarly defined either for a stick-type controller 1 or a pad-type controller 1.

In the case where the operation buttons 41 and 42 are those which are displayed on the display screen 47, the face of the controller that contains the display screen 47 defines the manipulation surface 43. Alternatively, only the screen of the display screen 47 on which information is to be displayed may define the manipulation surface 43. In the case of displaying operation buttons on the display screen 47, a touch screen panel is to be additionally provided on the display screen 47. When a user touches the position of an operation button, the touch screen panel detects this position, whereby the operation button being displayed by software can function similarly to a hardware operation button.

In the case where the manipulation surface 43, the left side face (not shown), the right side face 44, the upper side face 45, the lower side face (not shown), and the rear face 46 are composed of a single surface, it is meant that the left side face (not shown), the right side face 44, the upper side face 45, the lower side face (not shown), and the rear face 46 merely define portions that are based on relative positioning from the manipulation surface 43.

In the case where the manipulation surface 43 is composed of a touch panel, the operation buttons 41 and 42 are inclusive of manipulation input indications which are displayed on the touch panel. In common terminology, a "button" shall be a projecting portion of an electrical switch to be pressed by a finger; in the present specification, however, an "operation button" means any piece of user-manipulated hardware and/or any manipulation input indication that is displayed on a touch panel. For example, the operation buttons 41 and 42 may be implemented as a digital joystick or an analog joystick, or a touch pad. In the present specification, operation buttons as a generic notion encompassing all of these will also be denoted as "manipulable portions".

(Electrode Positions)

Next, the positions of electrodes for biological signal measurement which are placed on the controller 1 will be described.

Figure 3A:
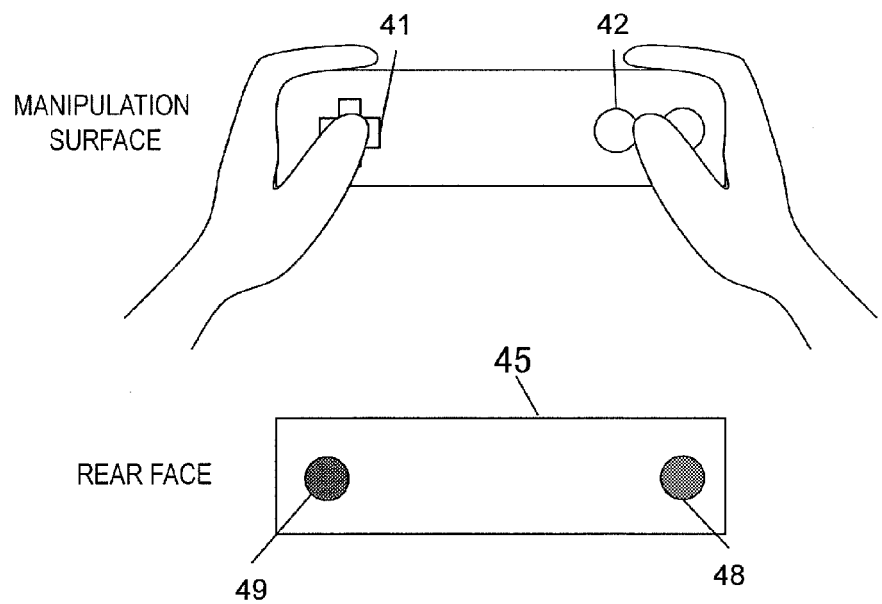
FIGS. 3A and 3B are diagrams showing examples of electrode positions in the case where electrodes are disposed on the rear face.
Figure 3B:
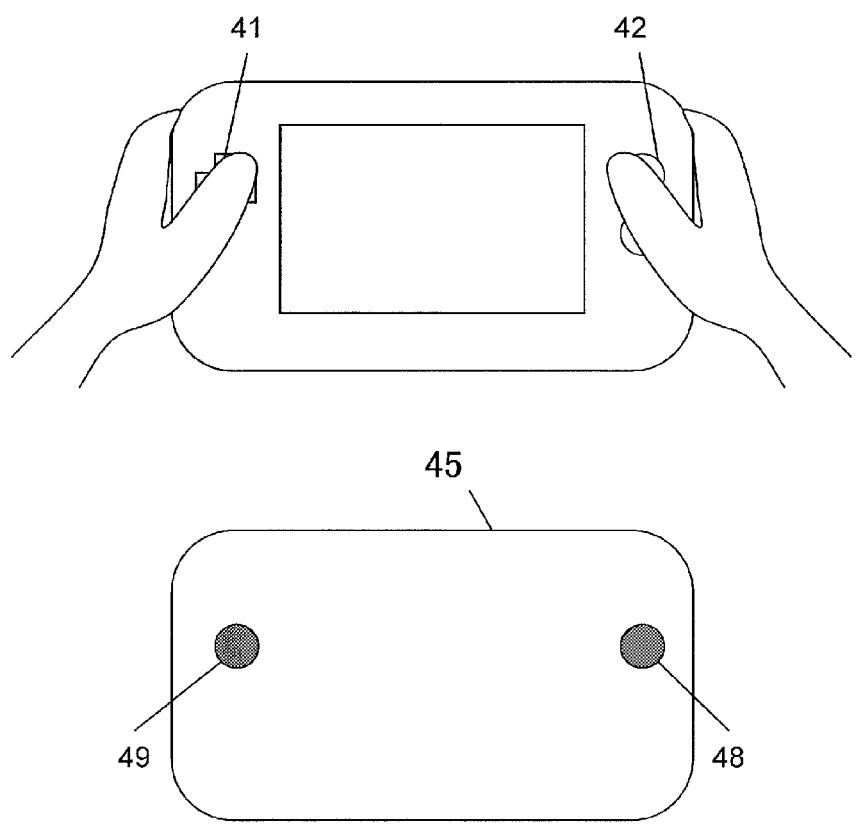

FIGS. 3A and 3B show examples where electrodes for biological signal measurement are placed on the rear face 46 of the controller 1.

In order to measure a biological signal, at least a plurality of electrodes are placed on the controller 1. In the present embodiment, a biological signal is detected as a potential difference between a plurality of positions at which a user is in contact with the controller. An example of a biological signal may be a potential difference between a finger of the right hand and a finger of the left hand, and may include a biological signal derived from an electrocardiogram, etc.

The user holds the stick-type controller 1 in both hands to manipulate the operation button(s) 41, 42 with a thumb. In doing so, in order to counteract the force with which the thumb presses the operation button(s) 41, 42, it is necessary to support the rear face 46 with an index finger or a middle finger. In order to support the rear face 46, the index finger or middle finger of the user stays in contact with the rear face 46.

The controller 1 has electrodes at positions where the user's fingers will come in contact the controller 1 when the user grips the controller 1.

For example, the rear face 46 has a plurality of electrodes each in a predetermined range which contains a position that is opposite from the position of the operation button(s) 41 or 42 on the manipulation surface 43. An example of a predetermined range is a range around the position opposite from the position of the operation button(s) 41 or 42, with a radius which is defined by the movable range of the user's finger.

The controller 1 shown in FIG. 3A includes an electrode 48 for the left hand at a portion where a finger of the left hand is in contact, and an electrode 49 for the right hand at a portion where a finger of the right hand is in contact.

Similarly with the pad-type controller 1 shown in FIG. 3B, the user supports the rear face 46 with fingers in order to counteract the force with which the operation buttons 41 and 42 on the manipulation surface 43 are pressed. The electrode 48 for the left hand and the electrode 49 for the right hand are placed at positions where the user comes in contact with the rear face 46 in order to support the rear face 46. By placing electrodes at these positions, biological signal measurement can be continued even during manipulation.

FIGS. 4A and 4B show examples where electrodes for biological signal measurement are placed on the upper side face 45 of the controller 1. One possible manner in which the user may hold the stick-type controller 1 in both hands is where the index fingers are placed on the upper side face 45, with the middle fingers, ring fingers, and little fingers being placed on the rear face 46.

In this case, the user's index fingers will stay on the upper side face 45 all the time, not just by way of supporting the rear face 46 to counteract the force with which the operation buttons 41 and 42 are pressed. Thus, the controller 1 may have the electrode 48 for the left hand and the electrode 49 for the right hand on the upper side face 45, where the index fingers are rested. Similarly a manner of holding in which the index fingers are rested on the upper side face 45 is also possible with a pad-type controller 1; therefore, the controller 1 may have the electrode 48 for the left hand and the electrode 49 for the right hand on the upper side face.

(Shapes and Number of Electrodes)

FIG. 5(a) to FIG. 5(d) show examples of electrode shapes. The electrode material is composed of an electrically conductive substance. An example of an electrode material is gold or silver. A desirable electrode material is a silver-silver chloride material because a silver-silver chloride material is not very susceptible to polarization when in contact with a living organism.

Other than the round-shaped electrode 51 of FIG. 5(a), which is similar to electrodes that are used for medical purposes, various shapes and numbers of electrodes may be employed depending on the application. For example, the number of electrodes that comes in contact with one hand does not need to be one; it may be two semicircular-shaped electrodes 52a and 52b as shown in FIG. 5(b), two electrodes 53a and 53b in the form of concentric circles as shown in FIG. 5(c), or three electrodes 54a, 54b, and 54c as shown in FIG. 5(d). Allocating two or more electrodes for each hand makes it possible to estimate the state of contact of each finger and the position of the finger, from how a signal is being acquired from each electrode.

Moreover, the electrode shape is not limited to a round shape. FIGS. 6A to 6C show other examples of electrode shapes. For example, as shown in FIG. 6A, electrodes may be placed in broad ranges around portions at which hands may come in contact, in order to ensure that contact will always be maintained. A band-shaped electrode (FIG. 6B) or multiple band-shaped electrodes (FIG. 6C) that expand not only on the rear face 46, but also to the upper side face 45 and the lower side face may be used to enable biological signal measurement against various manners of holding being envisaged.

(System Construction Diagram)

FIG. 7 shows a system construction for the information processing system 100. The controller 1 includes a manipulation input device 1a and a biological signal measurement device 1b.

The controller 1 receives a manipulation input made by the user, and also measures a biological signal of the user during the manipulation. Information including the measured biological signal is sent to the information processing apparatus 2.

Upon receiving inputs from the manipulation input device 1a or the biological signal measurement device 1b, the information processing apparatus 2 performs a predetermined process and outputs a result of the processing to the display screen equipment 3. The controller 1 and the information processing apparatus 2 are interconnected in a wireless or wired manner.

FIG. 8 shows the construction of the controller 1 and the information processing apparatus 2. A case where the controller 1 and the information processing apparatus 2 are wirelessly interconnected will be described.

The manipulation input device 1a in the controller 1 includes a manipulation input section 11 and a manipulation signal output section 12.

The manipulation input section 11 acquires or determines a manipulation signal which has been input from the operation button(s) 41 or 42. The manipulation information having been acquired is sent from the manipulation signal output section 12 to the information processing apparatus 2.

The biological signal measurement device 1b in the controller 1 includes an electrode section 13, a biological signal amplifier 14, and a biological signal output section 15.

The electrode section 13 is composed of a plurality of electrodes. The plurality of electrodes are placed at a position where the user's right hand comes in contact with the controller 1 and a position where the user's left hand comes in contact with the controller 1, for example.

The biological signal amplifier 14 amplifies a biological signal which corresponds to the potential difference between a plurality of electrodes. For example, a potential difference between the right hand and the left hand is amplified by the biological signal amplifier 14. The amplified signal is converted by an A/D converter into a digital signal, and this biological signal information is sent from the biological signal output section 15 to the information processing apparatus 2. Note that, when a biological signal can be measured to a certain potential or greater, the biological signal amplifier 14 does not need to amplify the biological signal, but may only measure the potentials at the plurality of electrodes. For this reason, the biological signal amplifier 14 may also be denoted as a biological signal measurement section in the following description.

In the information processing apparatus 2, the manipulation input information is received at a manipulation signal acquisition section 21, and the biological signal is received at a biological signal acquisition section 22, thus receiving the information from the controller 1.

While as a barely-recorded source signal, the biological signal is often not usable information. Therefore, the biological signal processor 23 performs a process of extracting meaningful information from the source signal. This corresponds to, for example, applying peak detection to chronological changes in a signal representing potential changes between both hands to thereby acquire heart rate information, for example.

The application processor 24 performs central processes of the information processing apparatus 2. Examples of application processing include: game progression in a game application; recording/data management/displaying in a health management application; question-giving/marking/result-displaying in a learning application, and so on. The application processing is realized by performing predetermined processes upon receiving an input from the controller 1. The application processor 24 may be a so-called application processor.

In order to feed the user back on the result of processing by the application processor 24, the display information output section 25 and the audio information output section 26 output a visual signal and an auditory signal. These output signals are sent to the display screen equipment 3.

The display screen equipment 3 reproduces the signals which have been output from the display information output section 25 and the audio information output section 26. As a result, the signals are presented to the user. Examples of the display screen equipment 3 include television sets, displays, and loudspeakers.

(Hardware Construction)

FIG. 9 shows the hardware construction of the controller 1. The controller 1 includes operation buttons 61, a control signal conversion circuit 62, a measurement electrode 63a, a reference electrode 63b, ground 63c, a biological amplifier 64, an AD conversion circuit 65, a transmission circuit 67, a signal processing unit 66, an antenna 68, and a battery 69.

Among these, the operation buttons 61 and the control signal conversion circuit 62 correspond to the manipulation input section 11 shown in FIG. 8. The measurement electrode 63a, the reference electrode 63b, and the ground 63c correspond to the electrode section 13 shown in FIG. 8, whereas the biological amplifier 64 corresponds to the biological signal amplifier 14 shown in FIG. 8. Note that the AD conversion circuit 65 may be included in the biological signal amplifier 14. The signal processing unit 66 includes a CPU 101, a RAM 102, a program 103, and a ROM 104. The transmission circuit 67 and the antenna 68 function as the biological signal output section 15 and/or the manipulation signal output section 12 show in FIG. 8; these may be referred to as the "output section" or "transmission section". These component elements are interconnected via a bus 105, so that mutual data exchange is possible. Power is supplied from the battery 69 to each circuit.

The press-down information of each of the operation buttons 61 is converted by the control signal conversion circuit 62, and sent to the CPU 101 via the bus.

The measurement electrode 63a, the reference electrode 63b, and the ground 63c are connected to the biological amplifier 64, these electrodes being mounted at predetermined places on the controller 1. The potential difference between the measurement electrode 63a and the reference electrode 63b is amplified by the biological amplifier 64, converted by the AD conversion circuit 65 from an analog biological signal to a digital signal, and, now as a biological signal that is capable of processing and transmission, sent to the CPU 101 via the bus.

The CPU 101 executes the computer program 103 which is stored in the memory 102. The computer program 103 describes a processing procedure as indicated by flowcharts which will be described later. In accordance with the computer program 103, the controller converts the manipulation signal and the biological signal which are sent from the antenna 68 via the transmission circuit 67. In certain cases, the program 103 may be stored in the ROM 104.

Note that the signal processing unit 66, the control signal conversion circuit 62, the transmission circuit 67, the biological amplifier 64, and the AD conversion circuit 65 may be implemented as a piece of hardware (e.g., a DSP) consisting of a semiconductor circuit having a computer program incorporated therein. Combining these into one semiconductor circuit will also provide the effect of reducing power consumption.

FIG. 10 shows the hardware construction of the information processing apparatus 2. The information processing apparatus 2 includes an antenna 71, a receiver circuit 72, a signal processing unit 73, an image control circuit 74, a display information output circuit 75, an audio control circuit 76, an audio information output circuit 77, and a power supply 78.

Among these, the antenna 71 and the receiver circuit 72 function as the biological signal acquisition section 22 and/or the manipulation signal acquisition section shown in FIG. 8. These may be referred to as the "reception section".

The signal processing unit 73 includes a CPU 111, a RAM 112, a program 113, and a ROM 114. The signal processing unit 73 functions as the biological signal processor 23 and/or the application processor 24 in FIG. 8. The image control circuit 74 and the display information output circuit 75 function as the display information output section 25 in FIG. 8. The audio control circuit 76 and the audio information output circuit 77 function as the audio information output section 26 in FIG. 8. These are interconnected via a bus 115 so that mutual data exchange is possible. Power is supplied from the power supply 78 to each circuit.

The manipulation information and biological information from the controller 1 are received by the receiver circuit 72 via the antenna 71, and sent to the CPU 111 via the bus 115.

The CPU 111 executes a computer program 113 which is stored in the memory 112. The computer program 113 describes a processing procedure as indicated by flowcharts which will be described later. In accordance with the computer program 113, the information processing apparatus converts the manipulation signal and the biological signal, performs a process for executing a predetermined application, and generates signals for providing image/audio feedback to the user. In certain cases, the program 113 may be stored in the ROM 114.

The image feedback signal which has been generated by the signal processing unit 73 is output from the display information output circuit 75 via the image control circuit 74, and the audio signal for feedback is output from the audio information output circuit 77 via the audio control circuit 76.

Note that the signal processing unit 73, the receiver circuit 72, the image control circuit 74, and the audio control circuit 76 may be implemented as a piece of hardware (e.g., a DSP) consisting of a semiconductor circuit having a computer program incorporated therein. Combining these into one semiconductor circuit will also provide the effect of reducing power consumption.

(Overall Flow of Processes)

FIG. 11 shows a flow of processes by the controller 1 and the information processing apparatus 2. Steps S11 to S14 illustrate internal processing by the controller 1, and steps S21 to S25 illustrate processing by the information processing apparatus 2.

<Step S11>

The manipulation input section 11 accepts a manipulation input. Specifically, at the timing of accepting a manipulation input, the manipulation input section 11 detects whether or not any operation button is being pressed. The timing of acceptance may be when an operation button is pressed down, for example.

<Step S12>

The manipulation signal output section 12 outputs a manipulation signal corresponding to the manipulation input accepted by the manipulation input section 11.

<Step S13>

The biological signal amplifier 14 measures a biological signal which corresponds to the potential difference between a plurality of electrodes of the electrode section 13. For example, a potential difference between the right hand and the left hand being in contact with the controller is measured. Moreover, the biological signal amplifier 14 may amplify the measured biological signal.

<Step S14>

The biological signal output section 15 outputs the biological signal.

Note that steps S11 and S12, and steps S13 and S14, may be conducted as a parallel process each. It is not necessary that the processes of steps S11 to S14 be executed all in this order.

<Step S21>

The manipulation signal acquisition section 21 receives the manipulation signal from the manipulation signal output section 12.

<Step S22>

The biological signal acquisition section 22 receives the biological signal from the biological signal output section 15.

<Step S23>

The biological signal processor 23 extracts biological information from the biological signal received at the biological signal acquisition section 22.

<Step S24>

Upon receiving the manipulation information from the manipulation signal acquisition section 21 and the biological information from the biological signal processor 23, the application processor 24 performs predetermined processes for executing the current application.

<Step S25>

In order to feed the user back on the result of processing by the application processor 24, the display information output section 25 outputs video information, and the audio information output section 26 outputs audio information.

Although not described in the flow of processes shown in FIG. 11, the display screen equipment 3 displays the information which is output from the information processing apparatus.

Note that the application processor 24 does not need to process both of the manipulation information from the manipulation signal acquisition section 21 and the biological information from the biological signal processor 23, and may process only the biological signal. In that case, step S21 of receiving the manipulation signal may be omitted.

(Embodiment 1)

The information processing system 100 of the present embodiment determines the orientation in which the controller is being held, through analysis of a bioelectric potential which has been measured by a bioelectric potential sensor that the controller includes.

The overall fundamental construction of the information processing system 100 of the present embodiment is as shown in FIG. 7 and FIG. 8. One of the characteristic features of the information processing system 100 of the present embodiment, i.e., the biological signal processor 23, will mainly be described.

FIG. 12 shows an exemplary construction of the information processing system 100 including the biological signal processor 23.

As shown in FIG. 12, the information processing system 100 at least includes the biological signal acquisition section 22, the biological signal processor 23, and the application processor 24. For example, the controller 1 at least includes the biological signal acquisition section 22 and the biological signal processor 23; the information processing apparatus 2 includes the application processor 24; and the information processing apparatus 2 subjects the processing result by the biological signal processor 23, included in the controller 1, to information processing.

The current bioelectric potential signal of the user which has been acquired by the biological signal acquisition section 22 is sent to the electrocardiographic component extractor 231. The electrocardiographic component extractor 231 extracts a predetermined electrocardiographic component, and the component direction determination section 232 determines whether the extracted electrocardiographic component is in the positive direction. Based on the result of determination, the button assignment change section 233 changes the assignment of operation buttons to control signals according to the particular manner of holding, and thereafter sends the information to the application processor 24. This realizes a control assignment to operation buttons that is adapted to the manner of holding. Hereinafter, the details thereof will be described with reference to flowcharts, data, etc.

FIG. 13 is a flowchart describing a flow of processes by the biological signal processor 23 shown in FIG. 12.

<Step S31>

The biological signal acquisition section 22 acquires a current bioelectric potential signal of the user which has been measured by using the electrode section that is placed on the housing composing the controller 1.

<Step S32>

The biological component extractor 231 extracts a predetermined electrocardiographic component. Now, an example of a signal which may be measured when the controller 1 is held in both hands, and an example of a predetermined electrocardiographic component will be described with reference to FIG. 14.

Portions (a) to (f) of FIG. 14 show two manners of holding the controller, examples of bioelectric potential signal corresponding to such manners of holding, and characteristic features of the respective waveforms. Portion (a) of FIG. 14 illustrates a case where the controller is held in "forward holding". Regarding the manners of holding the controller, the manner of holding in which an application under execution appears as originally expected is referred to as "forward holding", and the manner of holding in which the right hand and the left hand are reversed from what is considered normal or forward is referred to as "reverse holding". In forward holding, the moving direction designator button (cross-shaped operation button) 41 for the cursor is manipulated with the left hand, and the round button 42 is manipulated with the right hand. Conversely, in reverse holding as illustrated in portion (d) of FIG. 14, the controller is being held backwards, such that the cross-shaped operation button is manipulated with the right hand and that the round button 42 is manipulated with the left hand. In either manner of holding, electrodes for biological signal measurement are placed on the rear face 46, which is opposite from the manipulation surface 43, whereby a potential difference between both hands is measurable.

Examples of biological signals measured during forward holding and reverse holding, respectively, are shown in portions (b) and (e) of FIG. 14. A potential difference which is measured between both hands characteristically includes a signal of electrocardiographic origin, along with signals from the hands, arms, upper body, or other regions that are included in the paths to both hands. Since the heart is regularly pulsating, an electrical signal which is in synchronization with the pulses is generated, this signal being referred to as an electrocardiogram. Since this electrical signal is relative large among biological signals, there is an electrocardiographic component contained even in the fluctuations of potential difference between both hands. The electrocardiographic component is known to exhibit a waveform of a predetermined shape, whose characteristic features are denoted by symbols such as PQRST. Characteristic features of a waveform are describable based on these symbols. An example waveform change during one heartbeat is shown in portions (c) and (f) of FIG. 14 along with these symbols.

It can be seen that, although biological signals of substantially the same shape are being obtained in forward holding and in reverse holding, their waveforms undergo changes in opposite phases depending on which direction the heart is being measured (i.e., which orientation the controller is being held). In particular, it can be seen that the peak points, i.e., the Q point and the R point, are on opposites sides (i.e., on the upper or lower side) of the center line in the graph. For example, in portion (c) of FIG. 14, Q starts below the center line, and rapidly increases until registering the R point. In portion (f) of FIG. 14, on the other hand, the Q point starts above the center line, and rapidly decreases until registering the R point. The P, Q, R, S, and T symbols may be referred to as the P point, etc., when talking of their peak values, or the P wave, etc., when talking of the respective waveform that contains peak values.

The electrocardiographic component extraction which is performed by the biological component extractor 231 is an extraction of these peaking Q and R points. The Q point and R point have larger amplitudes than anywhere else, and thus can be easily extracted by setting an appropriate threshold value.

Alternatively, the biological component extractor 231 is able to distinguish between the positive direction and the negative direction based on the direction as to whether the T wave has an upward peak or a downward peak. Portion (c) of FIG. 14 shows an exemplary waveform in which the T wave has an upward peak. Portion (f) of FIG. 14 shows an exemplary waveform in which the T wave has a downward peak.

<Step S33>

FIG. 13 is referred to again. The component direction determination section 232 detects the direction of the electrocardiographic component which is extracted at step S32. For example, it determines whether the QR components are changing in the positive direction (Q<R) or in the negative direction (R>Q). The determination result will be either positive or negative.

By using a prestored criterion, the component direction determination section 232 determines the direction of the electrocardiographic component. An example of the prestored criterion is information of the magnitude range of the potential and the polarity of that potential. The polarity of a potential refers to the potential being positive or negative. When an electrocardiographic component having a potential matching a prestored criterion is extracted, the component direction determination section 232 determines it to be in the positive direction or the negative direction.

Another example of the prestored criterion is waveform patterns in the positive and negative directions. These patterns may be waveform patterns for different polarities as shown in portions (c) and (f) of FIG. 14 and (f), for example. The component direction determination section 232 determines a similarity between the waveform of the extracted electrocardiographic component and a prestored waveform pattern, and if a predetermined level of similarity or higher is detected, determines that the waveform is in the positive direction or the negative direction.

<Step S34>

The component direction determination section 232 makes a positive or negative determination. If the determination result is positive, control proceeds to step S37; if it is negative, control proceeds to step S35.

<Step S35>

If the direction of the QR component is negative, the component direction determination section 232 determines that the user has the controller in reverse holding, and sends this determination result to the button assignment change section 233.

<Step S36>

Based on the association between the operation buttons and the control information when determining that the user has the controller in reverse holding, the button assignment change section 233 changes the button assignment.

Portions (a) to (c) of FIG. 15 show examples of key assignment for forward holding and reverse holding. The controller 1 has a cross-shaped operation button 41 and round-shaped operation buttons 42 on the manipulation surface 43, so that, during forward holding, the cross-shaped operation button 41 are manipulated with the left hand and the round-shaped operation buttons 42 are manipulated with the right hand, as shown in portion (a) of FIG. 15. During reverse holding, the round-shaped operation buttons 42 are manipulated with the left hand, and the cross-shaped operation button 41 are manipulated with the right hand, as shown in portion (b) of FIG. 15. Assuming that up/down/right/left of the cross-shaped operation button correspond to A/B/C/D marks, the following assignment is adopted in reverse holding, as shown in the table of portion (c) of FIG. 15: 'down' is assigned to the A button; 'left' is assigned to the B button; 'up' is assigned to the C button; and 'right' is assigned to the D button.

Thus, even when the controller is held in the opposite orientation as shown in portion (b) of FIG. 15, up/down/right/left manipulations are properly realized, based on the particular manner of holding by the user as a criterion.

<Step S37>

If the direction of the QR component is positive, the component direction determination section 232 determines that the user has the controller in forward holding, and sends this determination result to the button assignment change section 233.

Thus, the operation buttons 41 and 42 are assigned to different manipulations depending on the manner of holding by the user. As shown in portion (c) of FIG. 15, for example, the assignment under forward holding and the assignment under reverse holding are different assignments. Thus, assignment information of the operation buttons 41 and 42 may be retained for each of a plurality of manners of holding. It will be appreciated that the same assignment of the operation buttons 41 and 42 may be applied for both two manners of holding.

<Step S38>

The button assignment change section 233 refers to prestored information that defines associations between manners of holding and operation button assignments to change the operation button assignment based on the manner of holding having been determined by the component direction determination section 232. For example, based on the associations between the operation buttons and control information when determining that the user has the controller 1 in forward holding, the button assignment may be changed. Specifically, as shown in portion (c) of FIG. 15, 'up' is assigned to the A button; 'right' is assigned to the B button; 'down' is assigned to the C button; and 'left' is assigned to the D button. Thus, even when the controller is held in the forward orientation as shown in portion (a) of FIG. 15, up/down/right/left manipulations are properly realized, based on the particular manner of holding by the user as a criterion.

In other words, in the present disclosure, different keybinds are applied depending on whether the user is found to have the controller in forward holding or reverse holding. A keybind is an assignment between manipulations and signals, defining which manipulation signal is to be output when each of a plurality of manipulable portions is manipulated. Depending on the positive or negative direction as determined by the component direction determination section 232, i.e., depending on the user's manner of holding, the assignment between each of a plurality of manipulable portions and each manipulation signal is varied.

<Step S39>

Based on the button assignment from the button assignment update section 233, the application processor 24 interprets the operation button(s) from the manipulation signal acquisition section 21 and executes an application.

Through the above processes, irrespective of whether the user has held the controller to his or her own liking or in the wrong manner, forward holding can be differentiated from reverse holding through analysis of a biological signal, and by applying a corresponding operation button assignment, the user is allowed to smoothly manipulate an application regardless of the orientation of the controller.

At S33, the component direction determination section 232 may only determine whether the electrocardiographic component is in the negative direction or not. In this case, if the electrocardiographic component is in the negative direction, the button assignment change section 233 changes the operation button assignment by referring to the prestored information that defines associations between manners of holding and operation button assignments. In other words, the button assignment remains unchanged if the electrocardiographic component is in the positive direction.

Alternatively, at S33, the component direction determination section 232 may only determine whether the electrocardiographic component is in the positive direction or not. In this case, if the electrocardiographic component is in the positive direction, the button assignment change section 233 changes the operation button assignment by referring to the prestored information that defines associations between manners of holding and operation button assignments. In other words, the button assignment remains unchanged if the electrocardiographic component is in the negative direction.

(Other Instances of Button Assignment)

Portions (a) to (f) of FIG. 16 show other instances of button assignment besides that shown in FIG. 15. Portions (a) to (c) of FIG. 16 show examples where two buttons, i.e., the E button and the F button, are disposed near both ends of the manipulation surface 43 of the controller 1. Portion (a) of FIG. 16 illustrates forward holding, and portion (b) of FIG. 16 illustrates reverse holding. In the case of reverse holding, the button assignment is exchanged between right and left, as shown in portion (c) of FIG. 16. Portions (d) to (e) of FIG. 16 show examples where the G button and the H button are disposed vertically on the manipulation surface 43 of the controller 1. Portion (d) of FIG. 16 illustrates forward holding, and portion (e) of FIG. 16 illustrates reverse holding. In the case of reverse holding, the button assignment is exchanged between up and down, as shown in portion (f) of FIG. 16.

FIG. 17A shows an instance of holding the controller 1 of FIG. 3B in portrait orientation. FIG. 17B shows the rear face 46 of the controller 1 in FIG. 17A. On the rear face 46, the controller 1 includes electrodes 51, 52, 53, and 54.

FIG. 17C and FIG. 17D show an instance of landscape orientation of the tablet-type controller 1, and electrodes on the rear face 46. FIG. 17E and FIG. 17F show an instance of portrait orientation of the tablet-type controller 1, and electrodes on the rear face 46.

As shown in FIG. 17C and FIG. 17D, the manner of holding the controller 1 can not only switch between right and left, but also between portrait and landscape orientations, as in the case of the tablet-type controller 1. Therefore, electrodes for bioelectric potential measurement are placed on the rear face 46 at four places of up/down/right/left. Without being limited to four electrodes, employing four or more electrodes enables distinction between two manners of holding under portrait orientation and two manners of holding under landscape orientation.

For example, in order to distinguish between two manners of holding under portrait orientation and two manners of holding under landscape orientation, prior to step S33 in FIG. 13, the component direction determination section 232 determines which at least two or more electrodes among the four electrodes the user is in contact with. By referring to a prestored relationship defining associations between electrode positions and manners of holding, the component direction determination section 232 may determine whether the user is holding the tablet-type controller 1 in portrait or landscape orientation, and thereafter determine whether it is in forward holding or reverse holding.

Moreover, without being limited to portrait orientation and landscape orientation, depending on the content of processing by the information processing apparatus 2, operation button assignments corresponding to other manners of holding the controller 1, e.g., the controller 1 being oblique held for manipulation. In this case, the component direction determination section 232 retains both information that defines associations between electrode positions which the user is in contact with and the user's manner of holding, and prestored information that defines associations between manners of holding and operation button assignments.

(Effect)

Thus, by measuring a bioelectric potential with a bioelectric potential sensor which is mounted on the controller 1 and analyzing the biological signal, it becomes possible to distinguish between forward holding and reverse holding. Either a right-handed person or a left-handed person may hold the controller simply in the direction that he or she prefers, and the operation button association will change accordingly, whereby an improved ease of use is provided. Moreover, even if the controller is held in the wrong manner, the controller will adopt a reversed association to provide the same manipulation feel as usual.

For example, even while the user is holding the controller at the same positions, the controller may vary in posture, tilt, etc. If the operation button assignment were changed based on the posture or tilt of the controller detected with a gyro sensor or the like, an unwanted change might occur in the button assignment. On the other hand, the controller according to the present disclosure assigns buttons by distinguishing the user's holding position and distinguishing between the right hand and the left hand, thereby providing a manipulation feel that enables manipulation without affecting the manipulation environment.

Moreover, the present disclosure is also effective for controlling screen rotation. For example, consider a case where a sitting user watches the screen of an electronic device of a tablet-type computer or the like, assuming that the tablet-type computer has a rectangular shape with longer sides and shorter sides. If the user is gripping the tablet-type computer in portrait orientation (i.e., its longer sides run the up-down direction), the user's face will be orientated substantially perpendicular to the ground in a usual state (sitting state), so that the direction interconnecting both eyes extends substantially parallel to the ground. Therefore, it would be valid, by relying on the output of a gyro sensor or the like which detects the orientation of the device relative to the ground, to adjust a displayed image on the tablet or the like (e.g., with respect to the orientation of the displayed text or image) so that it will always be displayed in the upper-to-lower direction along the longer sides. However, the user may then relax and lie down while continuing to grip the tablet in the same manner, and watch the displayed image on the tablet in that state. In this case, the manner of displaying should better be conserved because the user has not changed his or her way of gripping the tablet; however, the gyro sensor would output a signal indicating that the tablet has been rotated by about 90 degrees due to the user now lying down, thus causing the displayed image on the tablet to be rotated. This illustrates a problem where use of a mere gyro sensor output would induce a rotation control resulting in a direction that hinders reading. Conventionally, for example, a switch for explicitly prohibiting rotation is provided on the tablet, which needs to be manually turned ON/OFF by the user upon lying down. In the present disclosure, via detection of the manner of gripping, the displaying orientation is controlled so as to permit proper reading, by taking advantage of the fact that the manner of gripping is correlated with the face orientation.

Although a case is illustrated where the biological signal processor 23 is implemented within the information processing apparatus 2, its processing may occur inside the controller 1. The biological signal processor 23 may be provided immediately after the biological signal amplifier 14 in the controller 1, such that the biological signal processor 23 produces a result which is obtained by applying a button assignment update to the output from the manipulation signal output section 12. As a result, the controller will be able to distinguish between forward holding and reverse holding, and change the button assignment, all by itself. This can be realized by simply replacing the controller, without having to modify the information processing apparatus 2 per se.

(Embodiment 2)

Embodiment 1 mainly describes a distinction between forward holding and reverse holding which is performed inside the biological signal processor 23. While this construction allows to provide similar manipulation feels irrespective of the orientation in which the controller is held, incessantly making such determination would impose a continuous load on the processing of the information processing apparatus. Also, Embodiment 1 does not address issues such as the timing of a redetermination which will be needed when the user changes the manner of holding the controller, or passes the controller to another person.

The present embodiment illustrates an example where the timing of starting a manner-of-holding determination process relies on a biological signal analysis.

The overall fundamental construction of the information processing system according to the present embodiment is identical to the construction shown in FIG. 7 and FIG. 8. Therefore, the biological signal amplifier 14 and the biological signal processor 23, which are the differences from the construction of Embodiment 1, will mainly be described below.

FIG. 18 shows an exemplary construction for the biological signal amplifier 14 of the controller 1 and the biological signal processor 23 of the information processing apparatus 2 according to the present embodiment. In a state where both hands of the user are in contact with the electrode section 13, the potential amplifier 141 amplifies a potential difference between both hands, and the grip detector 142 determines whether or not a range within which the potential amplifier 141 is capable of amplification has been temporarily exceeded because of the user touching the electrodes anew. The A/D converter 143 converts the amplified analog signal into a digital signal. The biological signal acquisition section 22 receives a biological signal which is sent from the biological signal output section 15. The electrocardiographic component extractor 231, the component direction determination section 232, and the button assignment change section 233, which are within the biological signal processor 23, utilize the biological signal acquired by the biological signal acquisition section 22 to determine the direction in which the controller is gripped. By utilizing the determined direction of gripping the controller, the application processor 24 controls execution of application software. Note that the button assignment change section 233 may rely on an instruction from the application processor 24 to change the operation button assignment upon a manipulation input. For example, when deciding that the operation button assignment be updated based on the determined direction of gripping the controller, the application processor 24 sends information of the application software which is currently under execution to the button assignment change section 233. Receiving this information, the button assignment change section 233 changes the operation button assignment, based on what is to be executed by the application software. Instead of the information of what is to be executed by the application software, the button assignment change section 233 may directly receive information specifying an operation button assignment from the application processor 24.

FIG. 19 is a flowchart describing the timing of switching between two processes: a grip detection process of detecting the timing with which the user takes the controller 1 in his or her hand; and a manner-of-holding determination process that follows confirmation of a grip. In Embodiment 2, the process of awaiting the timing of grip and the process of manner-of-holding determination that follows confirmation of a grip are alternately performed, thus resulting in a continuum of processing. The current state of processing is stored as either one of the two modes of a grip detection mode and a manner-of-holding determination mode. Moreover, the flowchart of FIG. 19 is repetitively performed with a predetermined period, e.g., in synchronization with the communication period (several milliseconds to several dozen milliseconds) for game manipulations. Note that this communication period is an example. Depending on the characteristics of the application, the communication period may be about 100 milliseconds, or even greater.

<Step S40>

The grip detector 142 determines the current process mode. If the current process mode is the grip detection mode, control proceeds to step S41; if it is the manner-of-holding determination process mode, control proceeds to step S46.

<Step S41>

The grip detector 142 detects whether the user is not gripping the controller 1. It is a characteristic of bioelectric potential that, when the user has just gripped the controller 1 so that the electrodes come in touch with both hands, an excessive potential difference of an amplitude which goes beyond the measurable range will be input. By detecting this excessive amplitude, it is possible to detect a moment at which the electrodes are touched for the first time after the controller 1 has not been gripped by anyone. Specifically, for example, the output from the potential amplifier 141 may become saturated once exceeding the measurable range; by detecting this state of saturation, it is possible to determine a timing of grip.

Note that detection of a state of saturation is performed by utilizing an analog signal output of the potential amplifier 141. The A/D converter 143 does not perform A/D conversion until a grip is detected. Since incessant A/D conversion is avoided, power consumption can be reduced.

Portions (a) and (b) of FIG. 20 show examples of measured signals. In FIG. 20, (a) shows an example of measured bioelectric potential, and (b) shows switching of the process mode. At first, since the user is not gripping the controller 1, the signal that is measured in FIG. 20(*a*) is almost flat. Thereafter, from the moment (timing 261) at which the user grips the controller so that the electrodes on the controller rear face 46 come in touch with both hands, the measured potential rapidly increases to reach the maximum measurable value (timing 262). If this state is reached, it may be determined that a grip has occurred; if not, it may be determined that a grip has not occurred. Thus, grip detection is made.

<Step S42>

Depending on the determination result as to whether the user has gripped the controller 1 or not, control of the grip detector 142 branches out. If a grip by a user is detected, control proceeds to step S43; if not, control proceeds to step S45.

<Step S43>

Since the grip detector 142 has detected the user's grip of the controller 1, the association between the operation buttons and control is set to Assignment 1 for entering the manner-of-holding determination mode.

FIG. 21 is a correspondence table showing assignment between operation buttons and controls of an application which permits switching between right and left, in the case where the application under execution supports right-left holding. According to this table, during determination of the manner of holding, it is unclear as to which control should be assigned to which operation button. Therefore, as in Assignment 1 (reference numeral 271) in the correspondence table of FIG. 21, a "during determination" indication may be universally applied, for example. Thus, until determination is completed, the "during determination" indication on the screen provides the user feedback of the fact that a manipulation has been attempted, but that manipulation is not acceptable yet.

Alternatively, assignment of any control to the operation buttons may be spared during determination. Since the waiting time is only a short while until determination is finished, it will not be a problem if the pressing of an operation button(s) results in no operation being realized.

<Step S44>

Since the grip detector 142 has detected that the user is now gripping the controller 1, a manner-of-holding determination process needs to be performed in a subsequent run of this process. In order to store this fact, the process mode is switched to the manner-of-holding determination mode, and the process is ended.

<Step S45>

In the case where no change in the mode is needed, the grip detector 142 ends the process without performing any additional processes.

<Step S46>

Since the process mode is the manner-of-holding determination mode, the biological signal processor 23 performs a manner-of-holding determination process. The manner-of-holding determination process can be realized through a similar process to the determination process of FIG. 13. Through this process, the fact as to whether any information that enables determination of the manner of holding has been obtained, and, if a determination result is indeed obtained, the fact as to whether it is forward holding or reverse holding, are sent to the next step.

<Step S47>

Control of the biological signal processor 23 branches out depending on whether the manner-of-holding determination process has produced a determination result. If no determination result is obtained, control proceeds to step S45 in order to continue on the determination process; if a determination result is obtained, control proceeds to step S48 in order to change the operation button assignment.

As shown in FIG. 20, when an excessive potential difference is fed to the bioelectric potential sensor, the measurable range of the sensor will be exceeded, thus triggering an unmeasurable period of a certain length (timing 262 till timing 263). This unmeasurable period will vary depending on the sensor performance, and how the person's body is charged. Even after the ability to measure is resumed, a waiting time (timing 263 till timing 264) needs to be observed until a characteristic electrocardiographic component such as the R wave is detected, and thus the manner-of-holding determination process needs to be continued.

<Step S48>

In accordance with the result of manner-of-holding determination, the button assignment change section 233 of the biological signal processor 23 sets an assignment between operation buttons and controls. In the example of FIG. 21, Assignment 2 (reference numeral 272) is assigned for forward holding, and Assignment 3 (reference numeral 273) for reverse holding.

<Step S49>

Having performed its function, the button assignment change section 233 switches the process mode to the grip detection mode. Thus, the next timing of grip is awaited, e.g., the user taking the controller 1 in his or her hand afresh, or the user passing the controller to another user.

(Effect)

Through the above processes, by detecting a grip of the controller based on a change in the biological signal, an assignment of the operation buttons that conforms to the manner of holding can occur with an appropriate timing, while the user goes through instinctive motions.

Although Embodiment 2 illustrates an application which supports both right-handedness and left-handedness, the present technique is also effective in the case of a right-handed only application. FIG. 22 shows an assignment table in the case of a right-handed only application. A default assignment is already given as Assignment 1 (reference numeral 281) during the manner-of-holding determination period. After a determination result is obtained which points to Assignment 2 (reference numeral 282), if reverse holding is detected, then Assignment 3 (reference numeral 283) dictates that an indication "You are holding it backwards" be made on the screen, for example. As a result, the user is prompted to switch to the correct manner of holding.

Although the present specification illustrates an example where the operation buttons are buttons that can be physically depressed, similar changes of assignment will also be effective for icons which do not accept physical depression.

For example, similar processes will also be possible for icons that are drawn on a screen that has a touch panel, where the icons can be rearranged in an orientation of one's liking, for example.

In Embodiment 1, in accordance with the orientation in which the user holds the controller at the beginning, the assignment of every operation button is switched between forward holding and reverse holding as shown in FIG. 15. However, when a game or the like is manipulated over a long time, repeating similar button manipulations may cause finger fatigue. For example, when a car racing game is being played under forward holding as shown in FIG. 23(a), the cross-shaped operation button (cross keys) may often be used for the right-left control of the car, while the two buttons may be used for accelerator/brakes manipulations. In this case, the left hand will be used for controlling the car direction, while the accelerator/brakes manipulations will be performed with the right hand. In the case of a racing game, the accelerator button is likely to be continuously pressed down, thus causing fatigue in the right hand.

For this reason, the user may desire to switch the roles of the right and left hands. If reverse holding is consequently chosen as shown in portions (b-1) and (b-2) of FIG. 23, the cross keys will be designated to enable right-left control of the car, while the controller assignment as to the accelerator/brakes may be set according to the user's own preference. Specifically, if the user changes the manner of holding the controller during game play, a screen seeking user confirmation as to the accelerator/brakes keys may be displayed, after which the actual key assignment of the accelerator/brakes keys may take place. In FIG. 23, (b-1) and (b-2) show examples of key assignment.

Although changes of button assignment in accordance with forward holding or reverse holding are illustrated in Embodiment 1, a controller which is equipped with a display screen will also require an image reversal. For example, as shown in FIGS. 24A and 24B, images will be displayed in different directions depending on forward holding (FIG. 24A) and reverse holding (FIG. 24B). Note that an attitude sensor such as a gyro sensor may be provided for the controller 1, and a detection result by the sensor may be utilized in the determination of forward holding or reverse holding, together with a biological signal. As a result, the accuracy of determination as to forward holding or reverse holding can be improved.

The above embodiment (e.g., FIG. 8) illustrates that the information processing apparatus 2 includes the biological signal processor 23, and that the biological signal processor 23 performs the respective processes of electrocardiographic component extraction, positive/negative direction determination of the electrocardiographic component, and button assignment change. However, these processes may alternatively be performed in the controller 1.

FIG. 25 shows a variant of the construction of FIG. 8. The information processing system according to this variant includes a controller 241 and an information processing apparatus 242. The controller 241 corresponds to the controller 1 in FIG. 8, and the information processing apparatus 242 corresponds to the information processing apparatus 2 in FIG. 8.

In this variant, the respective processes of electrocardiographic component extraction, positive/negative direction determination of the electrocardiographic component, and button assignment change are performed in the controller 241. Therefore, the biological signal processor 23, which was previously included in the information processing apparatus 2 (FIG. 8), is provided in the controller 241 according to this variant. Moreover, the biological signal output section 15 and the biological signal acquisition section 22 in FIG. 8 do not exist. The specific construction and operation of the biological signal processor 23 provided in the controller 241 are as shown in FIG. 12, and the descriptions thereof are omitted.

The controller 241 includes a manipulation input device 241a and a biological signal measurement device 241b.

A manipulation signal output section 2412 of the manipulation input device 241a receives a manipulation signal from the manipulation input section 11, and a signal representing rules of button assignment change from the biological signal processor 23. Then, the manipulation signal output section 2412 modifies the manipulation signal in accordance with the rules of button assignment change, and outputs the manipulation signal after conversion to the information processing apparatus 242.

The manipulation signal acquisition section 21 acquires a manipulation signal, and sends it to the application processor 24. The application processor 24 performs processing in accordance with the received manipulation signal. The ensuing processing has already been described.

For convenience of description, any constitution corresponding to the display screen equipment 3 (FIG. 1) is omitted from illustration in FIG. 25. The display screen equipment may or may not be included.

The above embodiments illustrate a stick type (FIG. 2A), a pad type (FIG. 2B), and a tablet type (FIG. 17B) as examples of the controller 1. However, these are examples. For instance, a controller 1 which is obtained by fitting a smartphone into an attachment is another possible example.

FIG. 26 shows an example controller 1 as a combination of an attachment 250 and a smartphone 251. Operation buttons 41 and 42 are provided on a manipulation surface 43 of the attachment 250, and electrodes (not shown) similar to those in FIGS. 3A and 3B or FIGS. 4A and 4B are provided on its rear face or upper side face. The display of the smartphone 251 corresponds to the aforementioned display screen 47. The attachment 250 and the smartphone 251 are connected in a wired or wireless manner, such that manipulations made with the operation buttons 41 and 42 are sent to the information processing apparatus 2 via a communications function which is provided on the smartphone 251 or the attachment 250. Such a controller 1 allows a user of the smartphone, which lacks the electrodes and the operation buttons 41 and 42, to play a game by utilizing electrodes and operation buttons only when he or she wishes.

FIG. 26 illustrates an attachment 250 which covers the entire side faces and rear face of the smartphone 251. However, this is an example. For instance, the operation buttons 41 and 42 may be displayed on the display screen 47 and an input function based on a touch screen panel may be realized, thereby eliminating the need for the operation buttons 41 and 42 as hardware. Then, a sheet member (not shown) which only partially covers the rear face or the upper side face of the smartphone 251 and which has electrodes provided thereon may compose a controller 1 together with the smartphone 251.

FIG. 27 shows the construction of an information processing system 200 as a variant of the information processing system according to Embodiment 1 or 2. In the information processing system 200, a smartphone 251 having an electrode 49 for the left hand and an electrode 47 for the right hand attached on its rear face functions as the controller 1 in FIG. 1. Moreover, a server device 262 which communicates with the controller 1, via a network 263 such as the Internet, functions as the information processing apparatus 2 in FIG. 1. Note that the display screen of display screen equipment 3 in FIG. 1 corresponds to the display screen 48 of the smartphone 251.

In the information processing system 200 as such, manipulations on the smartphone 251 are sent to the server device 262, and the server device 262 processes the user's manipulations and biological signal.

Based on the processing result, the server device 262 sends data for displaying on the display screen 48 of the smartphone 251 to the smartphone 251. The smartphone 251 receives this data, and displays it on the display screen 48. The user's manipulation and biological signal and the content of processing thereof are as described with reference to FIG. 8 and FIG. 11.

Instead of the controller 1 shown in FIG. 27, the controller 241 shown in FIG. 25 may be used. In that case, the biological signal is processed at the controller 241, and the manipulation signal is sent to the server device 262.

The above embodiments illustrate that electrodes are separately provided in addition to operation buttons. However, this is an example, too. The operation buttons and the electrodes may be integrated; for example, electrodes may be attached on the operation buttons, or operation buttons may be formed of an electrically conductive material.

With an information processing system according to the present disclosure, regardless of whether forward holding or reverse holding is applied to a controller with which to manipulate an information processing apparatus, consistent operability is provided as adapted to the user's preferred manner of holding. Thus, the present system is applicable to any information processing apparatus which requires manipulation of a controller with both hands. Specifically, the present system is applicable to any device which is coupled with a controller having a biological sensor, e.g., television sets, personal computers, game machines, smartphones, and mobile phones.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An electronic device in a housing to be gripped by a right hand and a left hand of a user, the electronic device having a plurality of manipulable portions, comprising:
    a first electrode and a second electrode placed at positions which come in contact with the right hand and left hand of the user gripping the housing;
    one or more memories; and
    circuitry, which in operation is configured to:
    extract an electrocardiographic component of the user from a potential difference between the first electrode and the second electrode;
    determine whether the electrocardiographic component extracted is in a positive direction or a negative direction by referring to a prestored criterion concerning electrocardiographic component potential; and
    in accordance with a result of the determination, provide an assignment between each of the plurality of manipulable portions and each of a plurality of manipulation signals generated in response to a manipulation of each of the plurality of manipulable portions, thereby assigning each of the plurality of manipulable portions to a respective manipulation signal of the plurality of manipulation signals under a first relationship when the result of determination indicates the positive direction, and assigning each of the plurality of manipulable portions to a respective manipulation signal of the plurality of manipulation signals under a second relationship when the result of determination indicates the negative direction, the second relationship being different from the first relationship.

2. The electronic device of claim 1, wherein an R wave is extracted as the electrocardiographic component.

3. The electronic device of claim 2, wherein the circuitry is configured to further extract a Q wave as the electrocardiographic component, and distinguishes between the positive direction and the negative direction based on a direction of change of the QR component.

4. The electronic device of claim 1, wherein,
    the circuitry is configured to extract a T wave as the electrocardiographic component; and
    distinguishes between the positive direction and the negative direction based on whether the T wave has an upward peak or a downward peak.

5. The electronic device of claim 1, comprising a moving direction designator button for a cursor, wherein
    the circuitry is configured to provide assignment between directions on the moving direction designator button and the respective manipulation signals.

6. The electronic device of claim 5, wherein,
    the moving direction designator button is a button comprising manipulable portions among the plurality of manipulable portions, capable of moving the cursor in four directions of up, down, right, and left; and
    the circuitry is configured to
    assign to a first manipulable portion of the moving direction designator a first manipulation signal corresponding to an upward manipulation and assign to a second manipulable portion of the moving direction designator a second manipulation signal corresponding to a downward manipulation, under the first relationship, or
    assign to the second manipulable portion of the moving direction designator the first manipulation signal corresponding to the upward manipulation and assign to the first manipulable portion of the moving direction designator the second manipulation signal corresponding to the downward manipulation under the second relationship.

7. The electronic device of claim 5, wherein,
    the moving direction designator button is a button comprising manipulable portions among the plurality of manipulable portions, capable of moving the cursor in four directions of up, down, right, and left; and
    the circuitry is configured to
    assign to a first manipulable portion of the moving direction designator a first manipulation signal corresponding to a leftward manipulation and assign to a second manipulable portion of the moving direction designator a second manipulation signal corresponding to a rightward manipulation under the first relationship, or
    assign to the second manipulable portion of the moving direction designator the first manipulation signal corresponding to the leftward manipulation and assign to the first manipulable portion of the moving direction designator the second manipulation signal corresponding to the rightward manipulation under the second relationship.

8. The electronic device of claim 1, further comprising a grip detector for detecting a timing at which the user grips the housing with both hands, the timing being detected as a timing at which the potential difference between the first electrode and the second electrode becomes equal to or greater than a predetermined level.

9. The electronic device of claim 8, wherein the processes of extracting and determining begin at the timing.

10. The electronic device of claim 1, wherein,
after the process of determining has begun and until a result of determination is obtained, the circuitry provides the assignment between each of the plurality of manipulable portions and a manipulation signal to that of a predetermined relationship; and
after the result of determination is obtained, the circuitry provides the assignment between each of the plurality of manipulable portions and a manipulation signal to that of a relationship conforming to the result of determination.

11. The electronic device of claim 1, wherein the circuitry receives information of application software which is currently under execution, and accordingly changes the assignment.

12. The electronic device of claim 1, wherein the circuitry is configured to output to an external information processing apparatus the manipulation signal in response to a manipulation of one of the plurality of manipulable portions.

13. An information processing apparatus comprising:
one or more memories; and
circuitry, which in operation is configured to:
receive a manipulation signal from an electronic device having a plurality of manipulable portions;
acquire a biological signal of a user sent from the electronic device, the biological signal being a signal derived from a potential difference between a first electrode and a second electrode placed at positions which come in contact with a right hand and a left hand of the user gripping a housing of the electronic device;
extract an electrocardiographic component of the user from the acquired biological signal;
determine whether the extracted electrocardiographic component is in a positive direction or a negative direction by referring to a prestored criterion concerning electrocardiographic component potential; and
in accordance with a result of the determination, provide an assignment between each of the plurality of manipulable portions and each of a plurality of manipulation signals generated in response to a manipulation of each of the plurality of manipulable portions, thereby assigning each of the plurality of manipulable portions to a respective manipulation signal of the plurality of manipulation signals under a first relationship when the result of determination indicates the positive direction, and assigning each of the plurality of manipulable portions to a respective manipulation signal of the plurality of manipulation signals under a second relationship when the result of determination indicates the negative direction, the second relationship being different from the first relationship.

14. An information processing method using an electronic device,
wherein the electronic device is in a housing to be gripped by a right hand and a left hand of a user, the electronic device having a plurality of manipulable portions and a first electrode and a second electrode placed at positions which come in contact with the right hand and left hand of the user gripping the housing,
the method comprising:
extracting an electrocardiographic component of the user from a potential difference between the first electrode and the second electrode;
determining whether the electrocardiographic component extracted by the extracting step is in a positive direction or a negative direction by referring to a prestored criterion concerning electrocardiographic component potential; and
in accordance with a result of determination by the determining step, providing an assignment between each of the plurality of manipulable portions and each of a plurality of manipulation signals generated in response to a manipulation of each of the plurality of manipulable portions, so that each of the plurality of manipulable portions is assigned to a respective manipulation signal of the plurality of manipulation signals under a first relationship when the result of determination indicates the positive direction, and that each of the plurality of manipulable portions is assigned to a respective manipulation signal of the plurality of manipulation signals under a second relationship when the result of determination indicates the negative direction, the second relationship being different from the first relationship.

15. A non-transitory computer-readable medium having a computer program stored thereon to be executed by a computer mounted in an electronic device,
wherein the electronic device is in a housing to be gripped by a right hand and a left hand of a user, the electronic device having a plurality of manipulable portions and a first electrode and a second electrode placed at positions which come in contact with the right hand and left hand of the user gripping the housing,
the computer program causing the computer to execute:
extracting an electrocardiographic component of the user from a potential difference between the first electrode and the second electrode;
determining whether the electrocardiographic component extracted by the extracting step is in a positive direction or a negative direction by referring to a prestored criterion concerning electrocardiographic component potential; and
in accordance with a result of determination by the determining step, providing an assignment between each of the plurality of manipulable portions and each of a plurality of manipulation signals generated in response to a manipulation of each of the plurality of manipulable portions, so that each of the plurality of manipulable portions is assigned to a respective manipulation signal of the plurality of manipulation signals under a first relationship when the result of determination indicates the positive direction, and that each of the plurality of manipulable portions is assigned to a respective manipulation signal of the plurality of manipulation signals under a second relationship when the result of determination indicates the negative direction, the second relationship being different from the first relationship.

* * * * *